United States Patent
Yau

(10) Patent No.: US 9,605,295 B2
(45) Date of Patent: *Mar. 28, 2017

(54) ELECTROCHEMICAL SYSTEM AND METHOD THEREOF

(75) Inventor: Siu-Tung Yau, Solon, OH (US)

(73) Assignee: CLEVELAND STATE UNIVERSITY, Cleveland, OH (US)

( * ) Notice: Subject to any disclaimer, the term of this patent is extended or adjusted under 35 U.S.C. 154(b) by 777 days.

This patent is subject to a terminal disclaimer.

(21) Appl. No.: 13/533,248

(22) Filed: Jun. 26, 2012

(65) Prior Publication Data

US 2012/0267255 A1    Oct. 25, 2012

Related U.S. Application Data

(63) Continuation-in-part of application No. 12/267,423, filed on Nov. 7, 2008, now Pat. No. 8,585,879.

(Continued)

(51) Int. Cl.
| | |
|---|---|
| *C12Q 1/26* | (2006.01) |
| *C12Q 1/00* | (2006.01) |
| *G01N 27/327* | (2006.01) |

(52) U.S. Cl.
CPC ............ *C12Q 1/26* (2013.01); *C12Q 1/005* (2013.01); *G01N 27/3277* (2013.01)

(58) Field of Classification Search
CPC ............ C12Q 1/26–1/32; C12Q 1/005; G01N 27/3271–27/3278

(Continued)

(56) References Cited

U.S. PATENT DOCUMENTS

| | | |
|---|---|---|
| 4,721,601 A | 1/1988 | Wrighton et al. |
| 7,931,788 B1 * | 4/2011 | Wilkins ............... 204/403.02 |

(Continued)

FOREIGN PATENT DOCUMENTS

| | | |
|---|---|---|
| WO | WO 2005/075499 A1 | 8/2005 |
| WO | 2009/062099 A1 | 5/2009 |

OTHER PUBLICATIONS

International Search Report and Written Opinion of corresponding International Application No. PCT/US2013/047888, dated Feb. 19, 2014, 16 pages.

(Continued)

*Primary Examiner* — Luan Van
*Assistant Examiner* — Maris R Kessel
(74) *Attorney, Agent, or Firm* — Fay Sharpe LLP

(57) ABSTRACT

An embodiment of the invention provides an ultrasensitive and selective system and method for detecting reactants of the chemical/biochemical reaction catalyzed by an oxidoreductase, such as glucose and ethanol, at a concentration level down to zepto molar ($10^{-21}$ M). In embodiments, the invention provides an ampyometric immuno-sensing system comprising a working electrode, an oxidoreductase, and an external voltage generator, wherein the oxidoreductase is immobilized on the working electrode; and the voltage generator generates a voltage to induce an electric field that permeates at least a portion of the interface between the oxidoreductase and the working electrode. The ultrasensitivity of the system and method is believed to be caused by the electrical field, which enhances the quantum mechanical tunneling effect in the interface, and therefore facilitates the interfacial electron transfer between the oxidoreductase and the working electrode.

27 Claims, 20 Drawing Sheets

Related U.S. Application Data

(60) Provisional application No. 60/986,188, filed on Nov. 7, 2007.

(58) Field of Classification Search
USPC .... 204/403.01–403.15; 205/775, 777.5, 792; 435/7.1, 287.2, 287.9
See application file for complete search history.

(56) References Cited

U.S. PATENT DOCUMENTS

| | | | |
|---|---|---|---|
| 2004/0101741 A1 | 5/2004 | Minteer et al. | |
| 2004/0149577 A1 | 8/2004 | Kumar et al. | |
| 2006/0177870 A1* | 8/2006 | Tai-Tung et al. | 435/7.1 |
| 2009/0152129 A1 | 6/2009 | Yau | |

OTHER PUBLICATIONS

Gautham Kumar Ahirwal et al., "Gold nanoparticles based sandwich electrochemical immunosensor", Biosensors and Bioelectronics, vol. 25, No. 9, May 15, 2010 (May 15, 2010), pp. 2016-2020, XP055082548, ISSN: 0956-5663, DOI: 10.1016/j.bios.2010.01.029, abstract; scheme 1; fig. 1; chapter 2; p. 2017.

Jiapeng Wang et al., "Field-effect amperometric immuno-detection of protein biomarker", Biosensors and Bioelectronics, Elsevier BV, NL, vol. 29, No. 1, Jul. 28, 2011 (Jul. 28, 2011), pp. 210-214, XP028297841, ISSN: 0956-5663, DOI: 10.1016/J.Bios.2011.07.072, [retrieved on Aug. 4, 2011], abstract; fig. 1; chapter 2 and 4.

Xin Yu et al., "Protein inmunosensor using single-wall carbon nanotube forests with electrochemical detection of enzyme labels", Molecular Biosystems, vol. 1, No. 1, Jan. 1, 2005 (Jan. 1, 2005), p. 70, XP055082717, ISSN: 1742-206X, DOI: 10.1039/b502124c, abstract; scheme 1; p. 71, col. 1-p. 72, col. 1.

Milligan Christine et al., "Laccase based sandwich scheme immunosensor employing mediatorless electrocatalysis", Electroanalysis, vol. 14, No. 6, Apr. 2002 (Apr. 2002), pp. 415-419, XP002714249, ISSN: 1040-0397; the whole document.

Cuixia Ma et al., "Label-free sandwich type of inmunosensor for hepatitis C virus core antigen based on the use of gold nanoparticles on a nanostructured metal oxide surface", Microchimica Acta; An International Journal on Micro and Traceanalysis, Springer-Verlag, VI, vol. 178, No. 3-4, Jun. 9, 2012 (Jun. 9, 2012), pp. 331-340, XP035097845, ISSN: 1436-5073, DOI: 10.1007/S00604-012-0842-1, the whole document.

International Search Report for International Application No. PCT/US2008/082887.

Wang Gang et al: "Enzyme-immobilized $SiO_2$-Si electrode: Fast interfacial electron transfer with preserved enzymatic activity," Applied Physics Letters, AIP, American Institute of Physics, Melville, NY, vol. 87, No. 25, Dec. 16, 2005, pp. 253901-253901, XP012077023; ISSN: 0003-6951; abstract.

Kang et al., A novel glucose biosensor based on immobilization of glucose oxidase in chitosan on a glassy carbon electrode modified with gold-platinum alloy nanoparticles/multiwall carbon nanotubes, Analytical Biochemistry, vol. 369, Issue 1, Oct. 1, 2007, pp. 71-79.

Wang, G. et al: "Preserved enzymatic activity of glucose oxidase immobilized on an unmodified electrode," Electrochemistry Communication, Elsevier, Amsterdam, NL, vol. 8, No. 6, Jun. 1 2006, pp. 987-992, XP025182198; ISSN: 1388-2481; abstract.

Degani and Heller, "Direct electrical communication between chemically modified enzymes and metal electrodes. 1. Electron transfer from glucose oxidase to metal electrodes via electron relays, bound covalently to the enzyme", J. Physical Chemistry, Mar. 12, 1987, (91) 6, pp. 1285-1289.

Yau, Siu-Tung et al: "A prototype protein field-effect transistor," Applied Physics Letters, AIP, American Institute of Physics, Melville, NY, vol. 86, No. 10, Mar. 3, 2005, pp. 103508-103508, XP012064562, ISSN: 0003-6951, p. 103508-3, left-hand column, lines 31, 32, Figure 2.

* cited by examiner

ELECTROCHEMICAL SYSTEM AND METHOD THEREOF

This application is a continuation-in-part application based on U.S. patent application Ser. No. 12/267,423, filed Nov. 7, 2008, now U.S Pat. No. 8,585,879 which claims priority to U.S. Provisional Application No. 60/986,188, filed on Nov. 7, 2007, both of which are hereby incorporated herein by reference in its entirety.

BACKGROUND OF THE INVENTION

The present invention is generally related to an electrochemical system and method thereof. The system typically includes, but is not limited to, cyclic voltammetry (CV), linear voltammetry, pulse voltammetry, square wave voltammetry, amperometry, and the like. In exemplary embodiments, the invention relates to an amperometry/voltammetry system that includes an external voltage generator, and a method of detecting reactants of chemical/biochemical reactions catalyzed by a redox enzyme (also known as oxidoreductase).

The advent of nanotechnology has stimulated endeavors to develop detection techniques such as early disease diagnosis techniques through detecting small ensembles of molecules of substances, or even single molecules. For example, electrochemical detection using enzymes as sensing elements provides good substance selectivity due to the enzyme-analyte specific interaction. However, the intrinsic low level of interfacial charge transfer of this detection approach due to the embedment of enzymes' active sites by the protein environment creates a fundamental limit for the sensitivity of this approach.

Thus, there exists a continuing need for not only a selective but also a sensitive device, and a method useful for detecting target analytes.

Advantageously, various embodiments of the present invention provide an amperometry/voltammetry system including an external voltage generator; and a selective and ultrasensitive method using the system for detection of chemical/biochemical reactants at extremely low concentrations. The system and method provided may find application not only for known reactants, but also for the detection of emerging pathogens, for example those that may be generated or activated by changes in the environment, for example due to global warming.

BRIEF DESCRIPTION OF THE INVENTION

The present invention can be utilized to improve the sensitivity and detection limit of electrochemical detection systems, including amperometric and cyclic voltammetric systems. Such systems typically involve interfacial electron transfer between an electrode and the substance immobilized on the electrode, or the substance transiently in contact with the electrode through a process such as diffusion in solution phase. For example, the invention can be applied to amperometric immunosensing. The substance immobilized on the electrode, or the substance transiently in contact with the electrode, can be selected from inorganic and organic materials, bio-chemicals such as antigen and antibody systems, proteins, nucleic acid such as DNA, microorganisms and so on. The invention employs a gating voltage that generates an electric field at the electrode-solution interface to alter the electronic energy profile of the substance-electrode interface and hence to enhance the rate of quantum mechanical tunneling of charges from the substance to the electrode. The result is a field-induced enhancement of current flow between the electrode and the substance. The electrodes (gating electrode) used for applying the gating voltage can take various forms and can be made by various methods. As long as the field penetrates the sensing elements as indicated in FIG. 1, this technique achieves the desired goal. For example, the gating electrode may be in direct contact with the working electrode or may be spaced from the working electrode (not shown) and supported such that it is positioned for example above the working electrode.

In various embodiments of the invention, the sensing element, i.e. enzymes, nanoparticles, polymers, nanotubes, enzyme-labeled antigens and antibodies or microorganisms, is generally immobilized on an electrode. The field changes the electronic profiles or structures of the sensing element so that when the analyte diffuses from solution or gas to the electrode to be detected through a reaction with the sensing element, the electrons due to the reaction will be transferred into the electrode with higher rates. However, sometimes the sensing element i.e. an enzyme, is dissolved in solution. It reacts with the analyte to cause electron transfer between the analyte and the enzyme. Sometimes, the enzyme is reduced, meaning electrons are stored in the enzyme and need to be transported to the electrode. This can be done when the enzyme diffuses to the electrode and the field will assist the interfacial electron transfer. Alternatively, the enzyme requires chemicals called mediators to shuttle the electrons from the enzyme to the electrode.

CV can be used to probe the detection by finding the optimum cell potential. The cell potential is set at that optimum value and the cell current is measured as the signal (amperometry). One aspect of the invention provides a modified conventional electrochemical cell that can be used to perform cyclic voltammetry and amperometry. The cell comprises a reference electrode, an optional counter electrode and a working electrode, an oxidoreductase, and an external voltage (gating voltage) generator, wherein the oxidoreductase is immobilized on the working electrode; and the voltage generator generates a gating voltage that rearranges the ions in the sample solution at the electrode-solution interface and therefore induces an electric field that permeates at least a portion of the oxidoreductase that is in contact with the electrode.

Another aspect of the invention provides a method for detecting the reactant (or analyte) of a chemical reaction catalyzed by an oxidoreductase (or an enzyme or a general catalyst). The method uses a cyclic voltammetry or amperometry system that comprises a reference electrode, an optional counter electrode and a working electrode, an oxidoreductase, and a gating voltage generator, wherein the oxidoreductase is immobilized on the working electrode; and the voltage generator generates a gating voltage that rearranges the ions in the sample solution at the electrode-solution interface and therefore induces an electric field that permeates at least a portion of the oxidoreductase that is in contact with the electrode.

DETAILED DESCRIPTION OF THE INVENTION

Figure 1A:
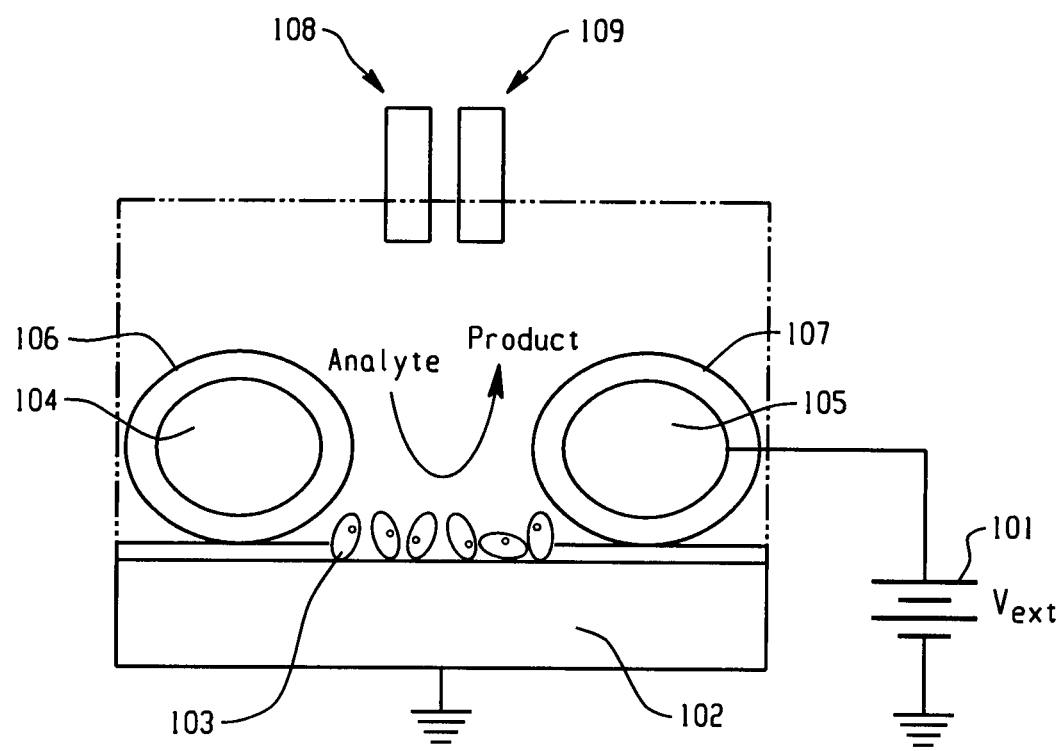
FIG. 1A shows the scheme of a cyclic voltammetry/amperometry system according to one embodiment of the invention; (where $V_{ext}$ is the gating voltage)

In various embodiments, the present invention provides a modified conventional electrochemical cell that can be used to perform cyclic voltammetry and amperometry. The cell comprises a reference electrode, an optional counter electrode and a working electrode, an oxidoreductase, and an external voltage (gating voltage) generator, wherein the oxidoreductase is immobilized on the working electrode; and the voltage generator generates a gating voltage that rearranges the ions in the sample solution at the electrode-solution interface, thereby inducing an electric field that permeates at least a portion of the oxidoreductase that is in contact with the electrode.

In an embodiment, the detection system is constructed based on a conventional cyclic voltammetry system. In a cyclic voltammetry experiment, a voltage (the cell potential) is typically applied to a working electrode in solution versus a reference electrode (see below) and the current flowing at the working electrode is plotted versus the cell potential to generate the cyclic voltammogram (CV). Such CV may show the faradaic current response which is caused by a redox reaction. The measurement can be used to investigate the electrochemical properties of species in solution as well as at the electrode/electrolyte interface. For example, information about the redox potential and electrochemical reaction rates of the species can be obtained.

The current response is measured over a potential window, starting at an initial value and varying the potential in a linear manner up to a pre-defined limiting value. At a switching potential, the direction of the potential scan is reversed, and the same potential window is scanned in the opposite direction.

Typically, the cyclic voltammetry system also uses a reference electrode and counter electrode (also known as the secondary or auxiliary electrode), in addition to the working electrode. Such three-electrode system is preferred in the present invention because, for example, the electrical potential of reference is stable, and does not change easily during the measurement. The potential of the working electrode versus the reference electrode follows a linear ramping in time, i.e. potential vs. time, and the current of the working electrode produced by this ramping is measured. This data is then plotted as current vs. potential.

In exemplary embodiments, the oxidoreductase comprises an enzyme that catalyzes the oxidation or reduction of an analyte or reactant resulting in charge transfer across the enzyme-electrode interface.

In exemplary embodiments, the oxidoreductase comprises a general biological, organic or inorganic electro-active material that induces charge transfer at the interface between the electrode and the general electro-active material.

In exemplary embodiments, the conversion of glucose to $CO2$ by yeast, with the formation of alcohol as a product is accomplished. Yeast contains enzymes, which catalyzes the conversion. Exemplary uses of this aspect of the invention include the formation of alcohol, spirits, and even vinegar for use in the beverage and food industry.

According to the present invention, the oxidoreductase is an enzyme that catalyzes the transfer of electrons from one molecule (the reductant) to another (the oxidant). In various embodiments, the oxidoreductases can act on reductants comprising CH—OH group (alcohol oxidoreductases); aldehyde or oxo; CH—CH group (CH—CH oxidoreductases); CH—NH$_2$ group (amino acid oxidoreductases, monoamine oxidase); CH—NH group; NADH or NADPH; sulfur group; heme group; diphenols and related substances; hydrogen; CH or CH$_2$ groups; metal ions; iron-sulfur proteins; reduced flavodoxin; phosphorus or arsenic; X—H and Y—H (to form an X—Y bond); and the like. The oxidoreductases can also act on oxidant comprising peroxide (peroxidases); superoxide radicals; and the like.

In an embodiment, the enzyme, glucose oxidase (GOx) was used as the oxidoreductase. The enzyme binds to beta-D-glucose and aids in breaking the sugar down into its metabolites. GOx is a dimeric protein which catalyzes the oxidation of beta-D-glucose to form D-glucono-1,5-lactone which then hydrolyzes to gluconic acid. GOx can be used in biosensors to detect levels of glucose by keeping track of the number of electrons passed through the enzyme by connecting it to an electrode and measuring the resulting current.

In another embodiment, alcohol dehydrogenases are used as the oxidoreductase. Alcohol dehydrogenases (ADH) facilitate the interconversion between alcohols and aldehydes or ketones. In humans and many other animals, they serve to break down alcohols which could otherwise be toxic; in yeast and many bacteria, some alcohol dehydrogenases catalyze the opposite reaction as part of fermentation. For example, in humans, the enzyme is contained in the lining of the stomach and in the liver. It catalyzes the oxidation of ethanol to acetaldehyde: $CH_3CH_2OH+ NAD^+ \rightarrow CH_3CHO+NADH+H^+$.

The external (gating) voltage generator is used to induce an electric field, which permeates at least a portion of the oxidoreductase immobilized on the electrode.

In an exemplary embodiment, the external voltage generator, referred to herein interchangeably as a gating voltage generator, generates a gating voltage between an insulator-covered metal wire, the gating electrode, referred to herein interchangeably as an external electrode, and the working electrode to induce the electric field. Depending on factors such as the nature and concentration of the analyte, the permeating electrical field generally has varied field intensity. For example, for inorganic material, the field intensity may be up to about 1000 volt/cm. For biochemical material such as oxidoreductase, the average field intensity may range up to 10 volt/cm, such as from about 0.2 volt/cm to about 6.0 volt/cm, and preferably from about 0.4 volt/cm to about 3.0 volt/cm.

With reference to FIG. 1A, the scheme of a cyclic voltammetry/amperometry system according to one embodiment is illustrated. The elliptical structures 103 represent oxidoreductase such as glucose oxidase molecules immobilized on the working electrode 102. The system includes a counter electrode 108 and a reference electrode 109. The oxidoreductase's active center is indicated by the small circle within the molecule 103.

The system can comprise a conventional three-electrode electrochemical cell modified with an external voltage generator, which is connected to additional electrodes (gating electrodes) for applying a voltage (gating voltage) to the working electrode, which is immobilized with oxidoreductase molecules. Copper wires 104 and 105 covered with insulating paint 106 and 107 induce an electric field across the molecule due to the applied voltage $V_{ext}$ from e.g. a battery 101. In FIG. 1A, a 0.5 mm-diameter copper wire coated with paint was used as the electrode for applying the field induced by the external voltage source $V_{ext}$.

Figure 1B:
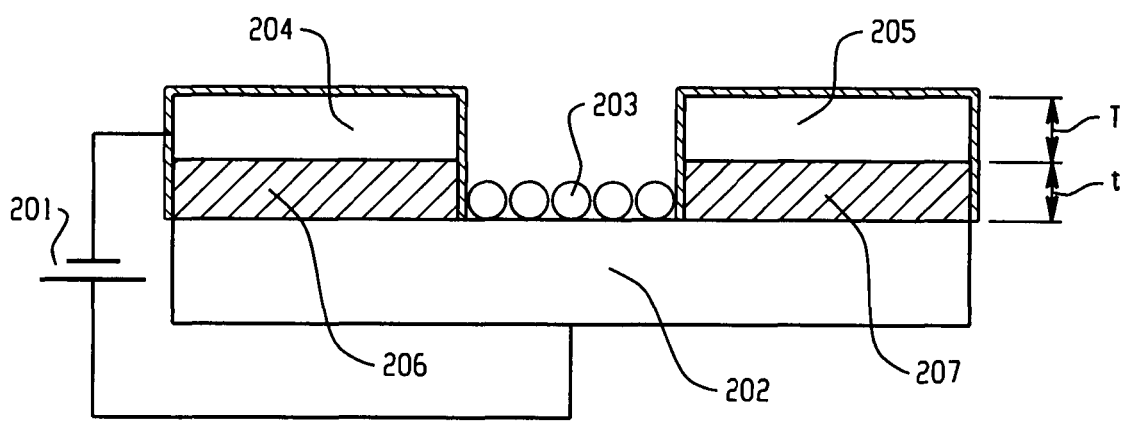
FIG. 1B shows the scheme of another cyclic voltammetry system according to one embodiment of the invention.

With reference to FIG. 1B, the scheme of another cyclic voltammetry/amperometry system according to one embodiment is illustrated. The circular structures 203 represent the sensing element such as oxidoreductase e.g. glucose oxidase molecules, immobilized on the working electrode 202. The system includes an optional counter electrode (not shown) and a reference electrode (not shown). The system can comprise a conventional three-electrode electrochemical cell modified with an external voltage generator and gating (metal) electrodes 204 and 205 with suitable thickness T for applying the gating voltage to the working electrode 202, which is immobilized with oxidoreductase molecules. Insulators 206 and 207 with suitable thickness t may be used between the working electrode 202 and gating electrodes 204 and 205. The gating electrodes 204 and 205 induce an electric field across the molecules due to the external voltage $V_{ext}$ from e.g. a battery 201.

$V_{ext}$ is the external (gating) voltage used to produce the electric field that permeates at least a portion of the oxidoreductase immobilized on the working electrode. Depending on factors such as the property of the electrode, the geometry of the electrode, the nature of the analyte, and the concentration of the analyte, $V_{ext}$ generally has a value of from about 0.001 volt to about 4 volt, preferably from about 0.005 volt to about 0.5 volt, and more preferably from about 0.01 volt to about 0.2 volt.

In various embodiments, the polarity of the permeating electric field is so designed that the additional electrode (e.g. the wire) is at a potential (e.g. Vext) higher than at the working electrode.

By applying an electric field to the enzyme molecules immobilized on the working electrode, the biocatalytic current of the cyclic voltammetry system is significantly enhanced, pushing the system's detection limit from the milli-molar ($10^{-3}$ M) range into the zepto-molar ($10^{-21}$ M) range with zepto molar detection resolution.

For example, glucose can be detected in the zepto molar ($10^{-21}$ M) concentration level, using the glucose oxidase as the sensing element. On this concentration level, there are only an extremely small number of glucose molecules in the sample solution, i.e., as few as 30 analyte molecules present. As a result, the system can respond distinctively to the incremental change in the number of analyte molecules in unit of 30 molecules.

In an embodiment, with a GOx-immobilized electrode, the field-induced increase in biocatalytic current has resulted in an 18-orders-of-magnitude improvement in the glucose detection limit. This effect allows the detection of glucose in the zepto-molar range with a detection limit of 50 zM. In another embodiment, this analyte detection approach has also been demonstrated with the ethanol-ADH system.

The detection limit shown in prior art systems is in the femto molar ($10^{-15}$ M) range. The present invention, however, shows that the detection limit can be in the zepto molar ($10^{-21}$ M) range, which is a $10^6$-fold improvement.

The system and method of the invention also exhibit very good analyte selectivity. For example, using the glucose-GOx system, the substance selectivity of the enzyme has not been compromised by the field.

The present invention can be widely used in industrial and academic applications. These include sensing of ultra-low concentration of harmful molecules in the environment, detection of small number of disease molecules in a patient's body fluid, and monitoring change of certain reactants in chemical reactions. The invention relies on the application of an electric field, which is readily induced by modifying an electrochemical cell with a gating electrode. The invention has direct applications in homeland security, food safety, early detection of emerging pathogens and diseases, and environment protection. In particular, in diabetes research, the detection of small number of 3β-hydroxybutyrate (3HB) will allow the doctor to issue early warnings for diabetes.

The following examples are included to provide additional guidance to those skilled in the art in practicing the claimed invention. The examples provided are merely representative of the work that contributes to the teaching of the present application.

EXAMPLE 1

A Cyclic Voltammetry Setting

As illustrated in FIG. 1A, enzyme-immobilized electrodes with a working area of about 1 mm×1 mm prepared by covering large enzyme-immobilized electrodes with a mask, were used as working electrodes for voltammetry measurements. A commercial Ag/AgCl (3 M KCl) electrode was used as the reference electrode, and a platinum wire was used as the counter electrode. The volume of the electrochemical cell was 1 ml. A scan rate of 50 mV/s was used in recording voltammograms.

Phosphate buffer solution (PBS) of 10 mM at pH 7 was used in the detection of glucose, while 100 mM PBS at pH 8.8 was used in the ethanol detection. The PBS was prepared using de-ionized water (18.2 MΩ cm). All measurements were made with deaerated PBS.

GOx (EC 1.1.3.4) from *aspergillus niger*, ADH (EC 1.1.1.1) from *saccharomyces cerevisiae* and the chemicals used in this work (beta-D(+)glucose with 97% purity, ethanol with >99.9% purity and sodium phosphate with >99.95% purity) were purchased from Sigma and were used as received.

The preparation of electrode and enzyme immobilization was carried out according to G. Wang, N. M. Thai, S. -T. Yau, Electrochemistry Communications 8, 987-992 (2006); G. Wang, N. M. Thai, S. -T. Yau, Biosensors and Bioelectronics 22, 2158 (2007); G. Wang, S. -T. Yau, APPLIED PHYSICS LETTERS 87, 253901 (2005); and G. Wang, S. -T. Yau, Journal of Physical Chemistry C., the entirety of which are incorporated herein by reference. For example, an edge plane graphite electrode was be prepared, and enzyme immobilization via incubation results in the formation of a monolayer of enzyme on the electrode as revealed by atomic force microscopy. Enzymes such as glucose oxidase ($GO_x$) and alcohol dehydrogenase (ADH) were immobilized individually on the bare edge-plane of highly oriented pyrolytic graphite (HOPG) electrodes via incubation.

It was shown that when GOx is immobilized on bare HOPG and silicon electrodes, its enzymatic activity is preserved. The attachment of $NAD^+$ to ADH was carried out by contacting the ADH-immobilized HOPG electrode with a $NAD^+$-containing solution, followed by rinsing with de-ionized water, as described in Y. Liu, F. Yin, Y. Long, Z. Zhang, S. Yao, Journal of Colloid and Interface Science 258, 75 (2003), the entirety of which is incorporated herein by reference.

The determination of detection limit was made according to signal/noise=3. Bare HOPG electrode did not respond to glucose and ethanol under the conditions of this work. The calibration curves were obtained using cyclic voltammetry/amperometry.

EXAMPLE 2

Measurement ($V_{ext}=0$) of Glucose with Different Concentrations

Figure 1C:
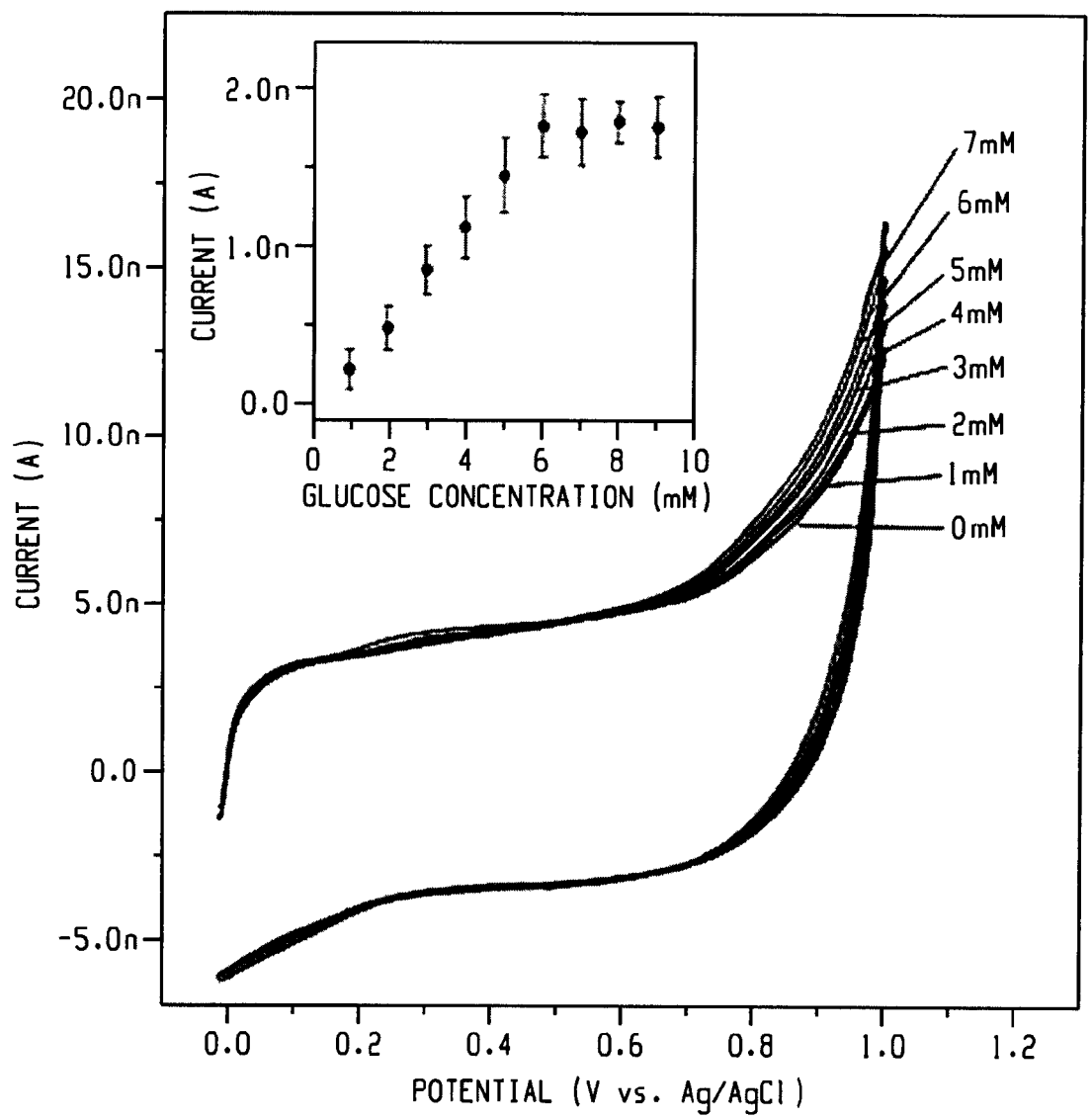
FIG. 1C shows the cyclic voltammograms (CV) and calibration curve (inset) of an electrode immobilized with glucose oxidase used to detect glucose with different concentrations without the permeating electric field according to one embodiment of the invention.

In this example, CVs were obtained with different glucose concentrations (from 0 to 7 mM). FIG. 1C shows the CVs and the calibration curve (inset) of an electrode immobilized with glucose oxidase used to detect glucose without an electric field. The detection is in the milli-molar range.

EXAMPLE 3

Measurement ($V_{ext}=0.15V$) of Glucose with Different Concentrations

Figure 1D:
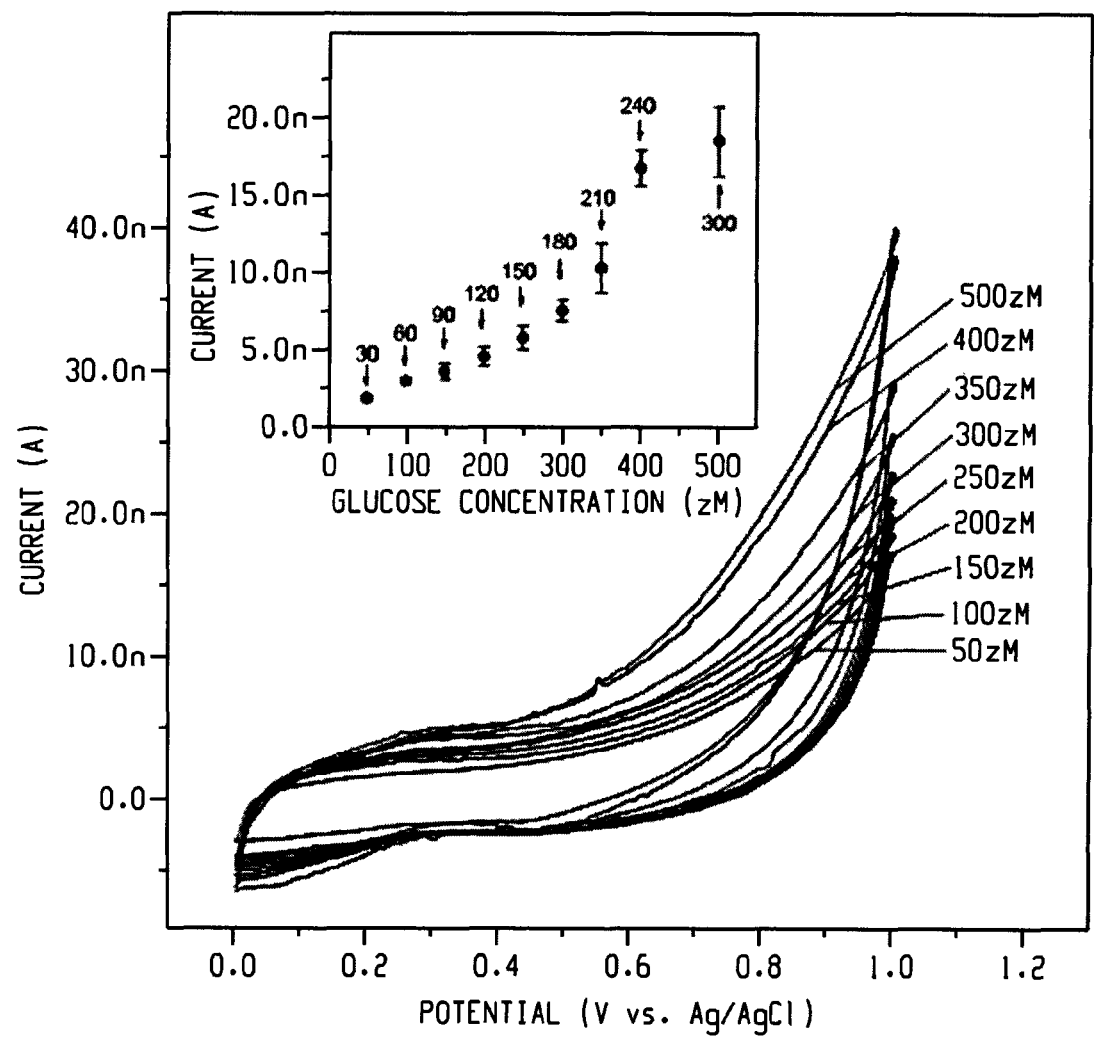
FIG. 1D shows the CVs and calibration curve (inset) of an electrode immobilized with glucose oxidase used to detect glucose with different concentrations with a permeating electric field generated by $V_{ext}=0.15V$ according to one embodiment of the invention.

FIG. 1D shows CVs and the calibration curve (inset) of the same electrode as in FIG. 1C. CVs were obtained with different glucose concentrations and with $V_{ext}=0.15V$. The number associated with each data point indicates the number of glucose molecules in the cell. FIG. 1D shows the detection of glucose with the application of $V_{ext}$ in the zepto molar range. Each glucose concentration corresponds to an extremely small number of glucose molecules in the sample. At this concentration level, the phrase "detection of single molecules" becomes plausible.

EXAMPLE 4

Measurement of 3 mM Glucose with/without $V_{ext}$

Figure 2A:
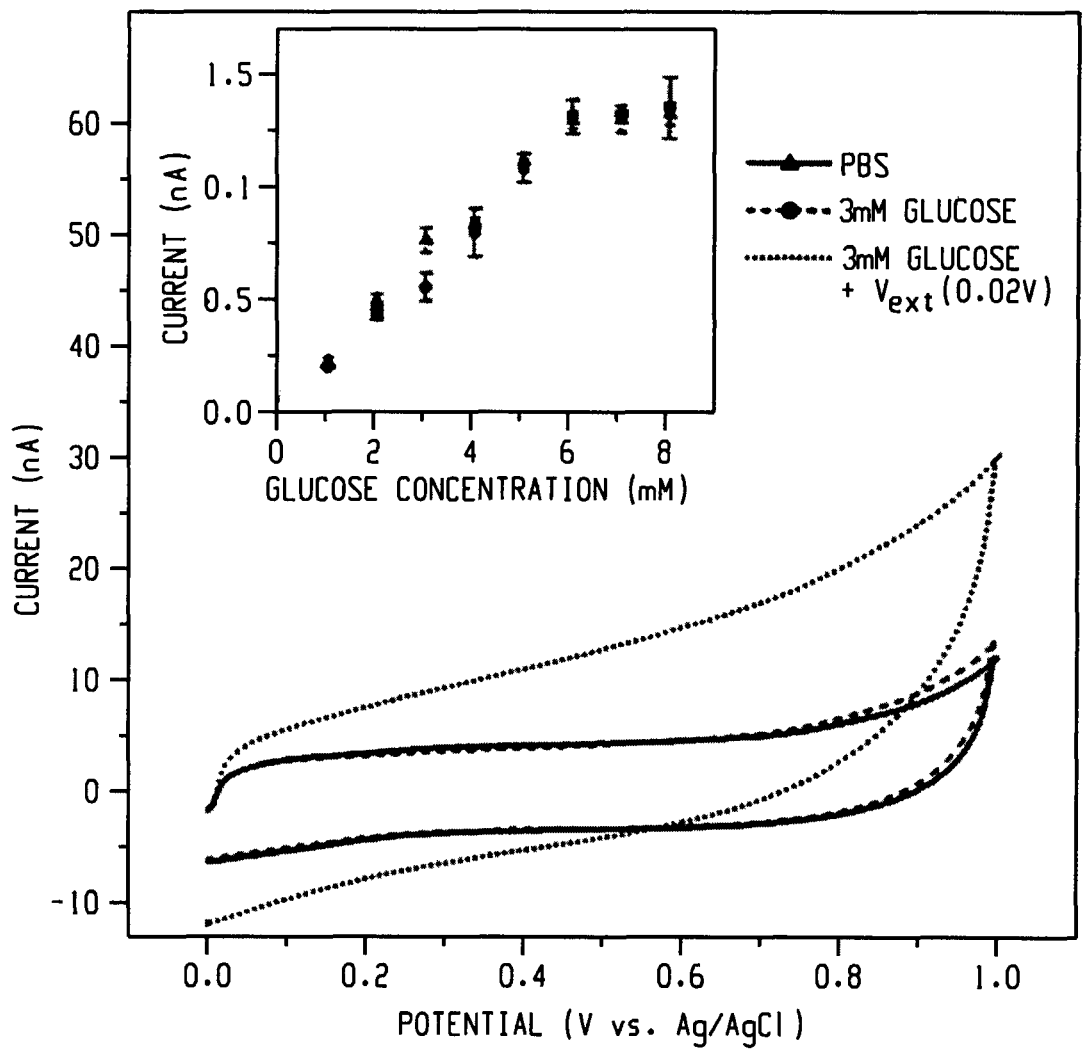
FIG. 2A shows the CVs of an electrode immobilized with glucose oxidase used to detect 3 mM glucose in the absence and presence of a permeating electric field generated by $V_{ext}=0.02V$ according to one embodiment of the invention.

The electrochemical response of a GOx-immobilized electrode to glucose was measured. In FIG. 2A, the solid line CV is the electrode's behavior in PBS (background signal). The dash line CV shows the electrode's response to 3 mM glucose. These CVs were obtained with $V_{ext}=0$. The dot line CV was obtained with $V_{ext}=0.02$ V at 3 mM of glucose.

The inset shows two glucose calibration curves of the electrode obtained when $V_{ext}=0$ but under different conditions. The 3 mM glucose curve was obtained before applying $V_{ext}$ to the GOx molecules. The PBS curve was obtained with $V_{ext}=0$ after $V_{ext}$ has been increased to 0.15 V and returned to 0 V. The current values are evaluated at the potential of 0.9 V and the background has been subtracted from the data points so that the data points show the glucose oxidation current. The curves indicate the Michaelis-Menten kinetic behavior of the biocatalytic process. The glucose detection limit of the electrode is 1 mM. When $V_{ext}$ was applied to the enzyme molecules by increasing $V_{ext}$ from zero, the glucose oxidation current was found to increase significantly for the same glucose concentration.

The application of $V_{ext}$ did not produce permanent or irreversible effect on the catalytic activity of the immobilized GOx. In the inset of FIG. 2A, the PBS curve shows that the electrode's response to glucose with $V_{ext}$ turned off after having been increased to 0.15V. The PBS curve almost coincides with the 3 mM gluscose curve, which was obtained before applying any electric field to the GOx molecules. Thus, the field used did not produce permanent detrimental effect on the catalytic activity of the GOx, and it is likely that the conformation of the enzyme remained unaltered.

EXAMPLE 5

Measurement of 8 mM Glucose with Different $V_{ext}$

Figure 2B:
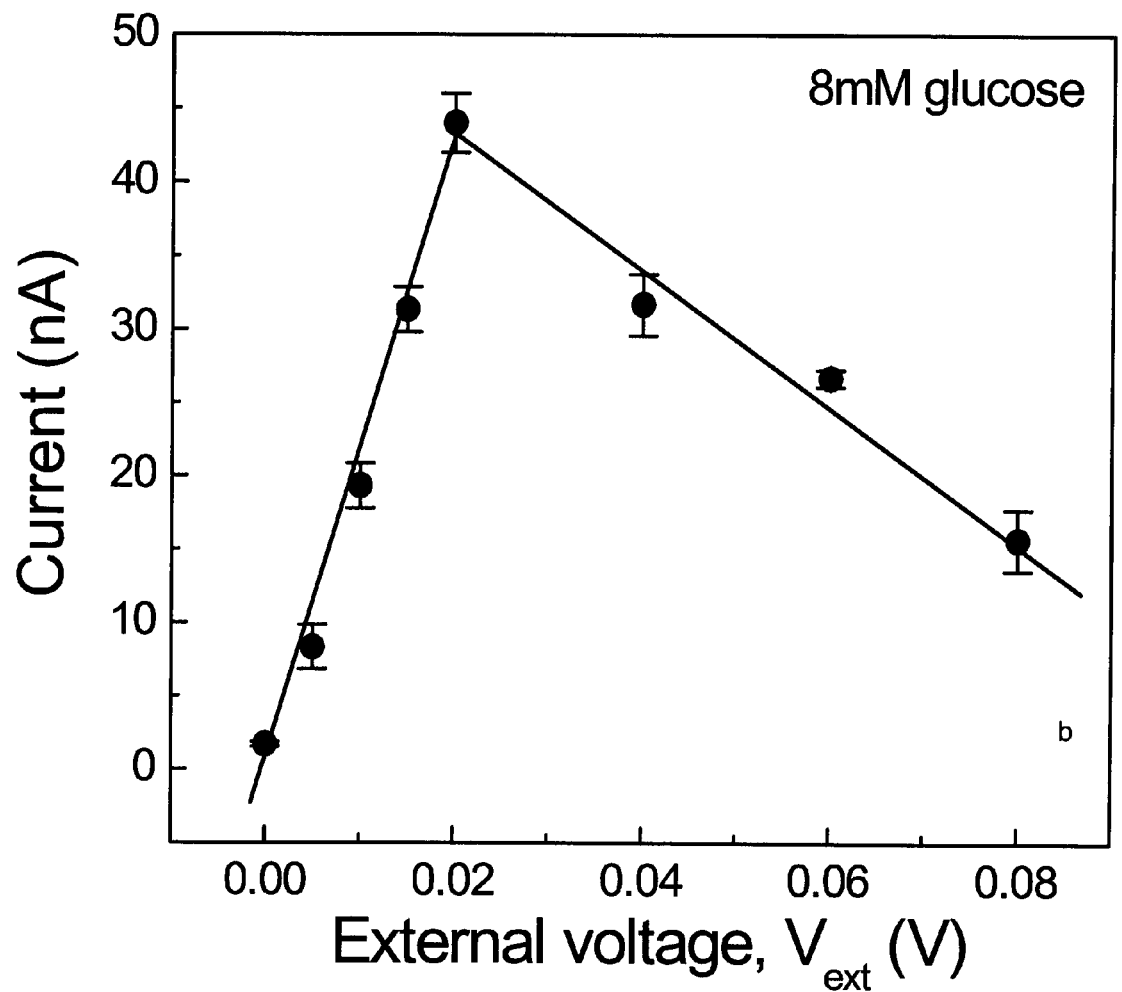
FIG. 2B shows the relation between the glucose oxidation current and $V_{ext}$ at 8 mM of glucose according to one embodiment of the invention.

FIG. 2B shows the field-induced enhancement in the oxidation current of glucose. With 8 mM of glucose, the oxidation current undergoes a 23-fold increase as $V_{ext}$ is increased from 0 to 0.02 V. Then, the current starts to decrease. FIG. 2B shows the relation between the glucose oxidation current and $V_{ext}$ at 8 mM of glucose. The currents were evaluated at a potential of 0.9 V. The background current has been subtracted. The critical voltage $V_c$ occurs at about 0.02V.

EXAMPLE 6

Measurement ($V_{ext}$=0.12V) of Glucose with atto-Molar Concentrations

Figure 3A:
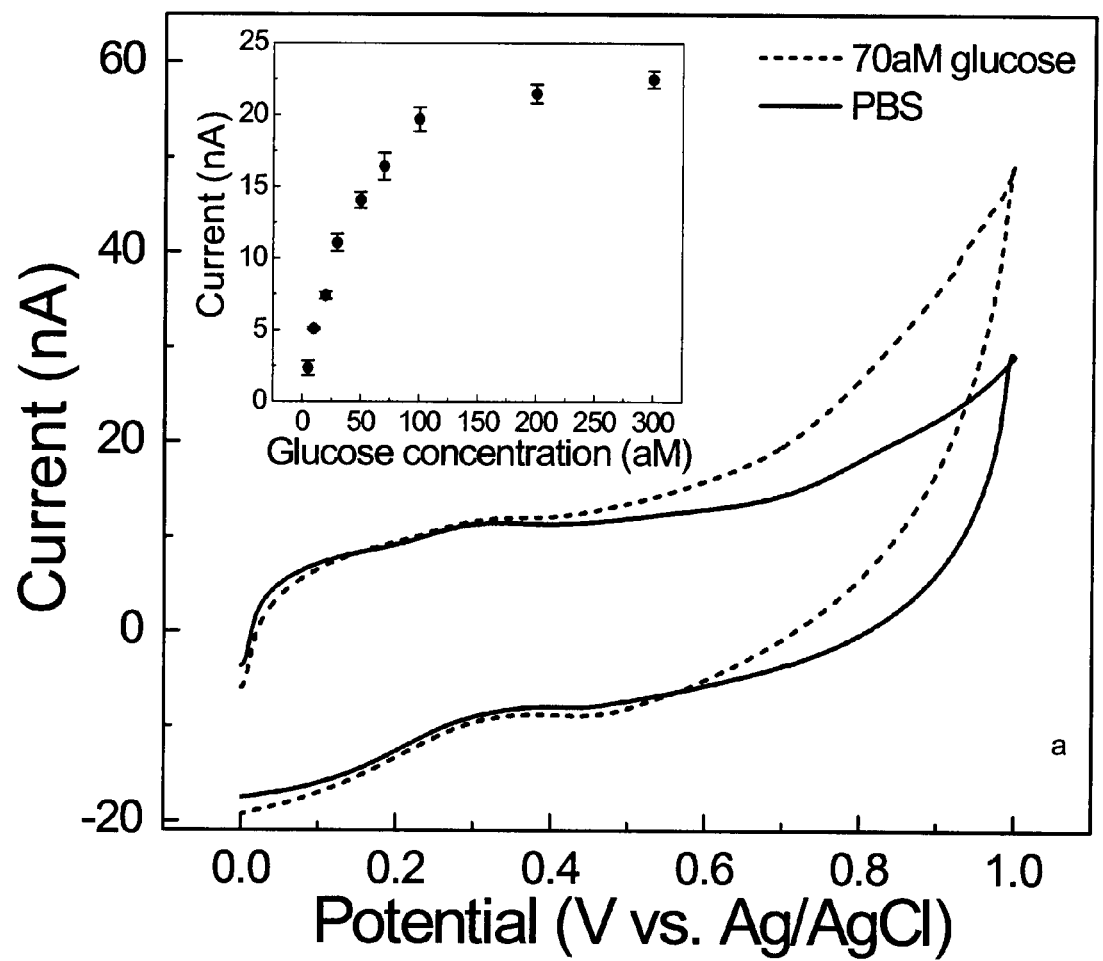
FIG. 3A shows the CVs of a GOx-immobilized electrode in PBS and 70 aM glucose with $V_{ext}=0.12$ V; and the inset shows the calibration curve of the electrode in the atto-molar range of glucose according to one embodiment of the invention.

Examples 6-10 show field-induced enhancement in analyte detection. In FIG. 3A, the solid line CV shows the behavior of a GOx-immobilized electrode in PBS. The dash line CV is the electrode's response to 70 aM glucose. These CVs were obtained with $V_{ext}$=0.12 V. The inset shows the calibration curve of the electrode in the atto-molar range of glucose. The current values were evaluated at the potential of 0.9 V and each point is the difference between the measured current and the corresponding current on the solid line CV so that the data point shows the glucose oxidation current.

The effect described above allowed us to detect glucose at progressively lower concentrations below the milli-molar range by increasing $V_{ext}$. FIG. 3A shows the field-induced glucose detection in the atto-molar ($10^{-18}$ M) range with $V_{ext}$=0.12 V. The calibration curve in the inset shows that the detection limit under this particular condition is 5 aM with a detection resolution of 10 aM.

EXAMPLE 7

Measurement ($V_{ext}$=0.15V) of Glucose with Zepto-Molar Concentrations

Figure 3B:
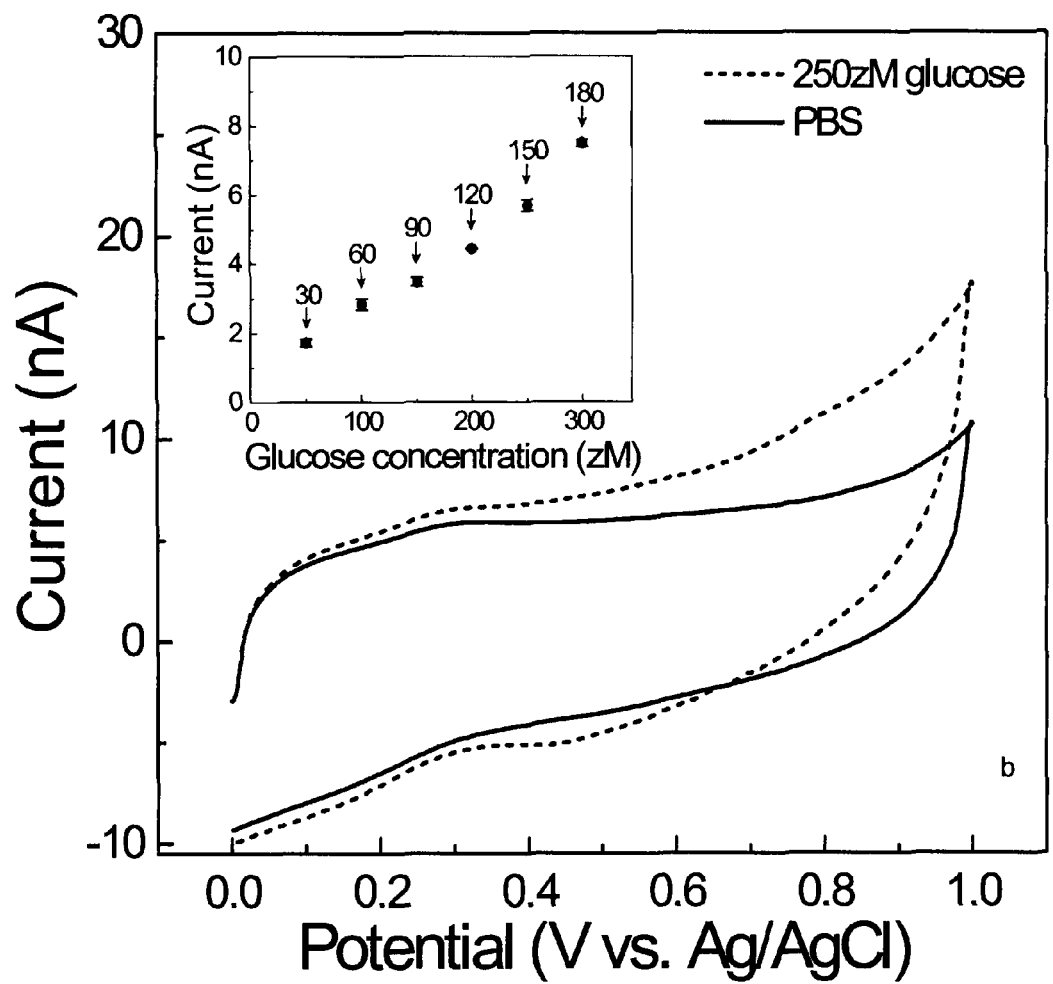
FIG. 3B shows the CVs of a GOx-immobilized electrode in glucose of zepto-molar ($10^{-21}$ M) concentration range with $V_{ext}=0.15$ V according to one embodiment of the invention.

Detection of glucose in the zepto-molar ($10^{-21}$ M) concentration range was obtained with $V_{ext}$=0.15 V as shown in FIG. 3B. The calibration curve in the inset shows a detection limit of 50 zM with a detection resolution of 50 zM. The error bars show that the current of each data point distinctively represents the corresponding concentration. Considering the volume of the cell, each data point can be associated with the number of glucose molecules in the cell, as indicated by the numbers associated with each data point in the inset. In particular, the system was able to detect 30 glucose molecules present in the cell and showed response to each incremental change in the unit of 30 glucose molecules in the cell.

In FIG. 3B, the solid line CV shows the behavior of a GOx-immobilized electrode in PBS (the background). The dash line CV is the electrode's response to 250 zM glucose. These CVs were obtained with $V_{ext}$=0.15 V. The inset shows the calibration curve of the electrode in the zepto-molar range of glucose. The current values were evaluated at the potential of 0.9 V and each data point shows the glucose oxidation current with the background subtracted.

EXAMPLE 8

Figure 3C:
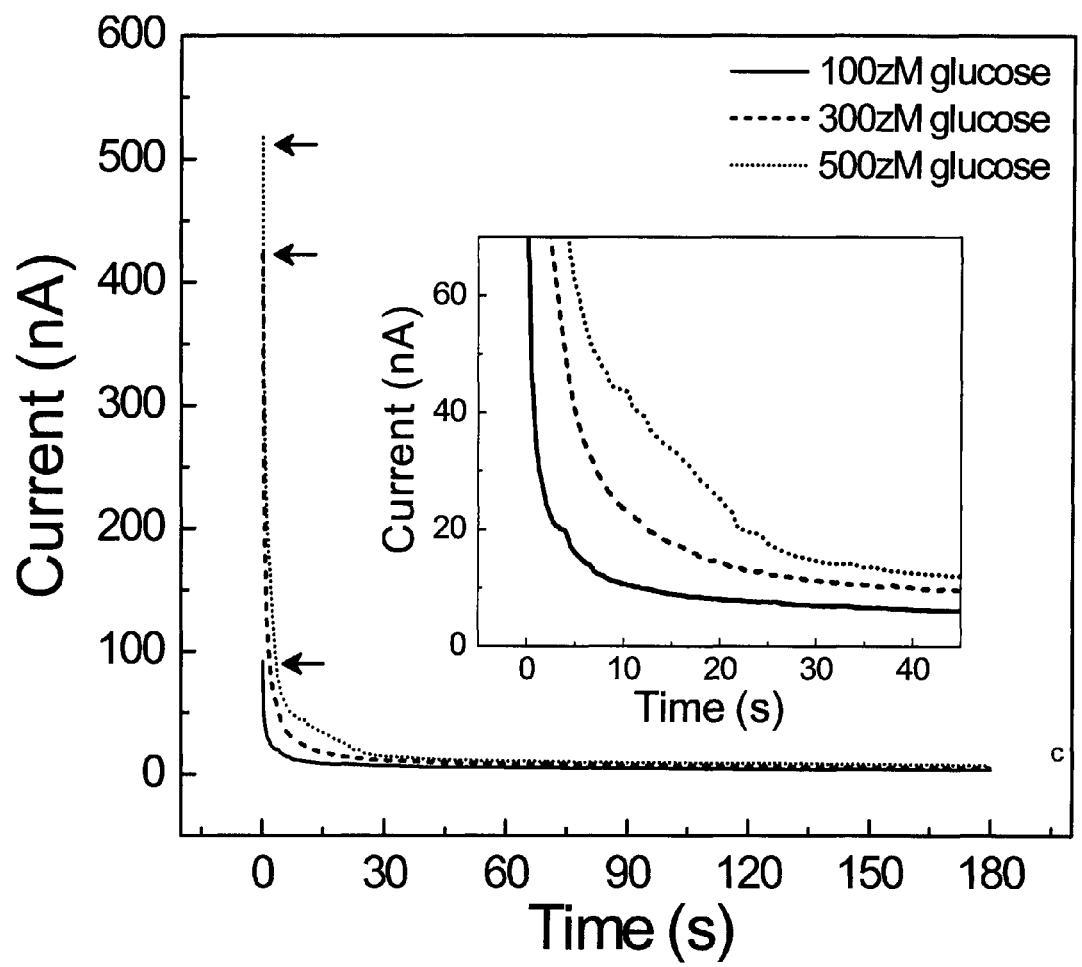
FIG. 3C shows the temporal decay of oxidation current of a GOx-immobilized electrode in glucose with zepto-molar concentrations with $V_{ext}=0.15$ V according to one embodiment of the invention.

Current vs. Time Measurement ($V_{ext}$=0.15V) of Glucose with Zepto-Molar Concentrations In FIG. 3C, the current of the electrode as in FIG. 3A was monitored over time in different glucose concentrations in the zepto-molar range at a potential of 0.8 V and with $V_{ext}$=0.15 V. The arrows indicate the initial current for each glucose concentration. The inset shows the details of the temporal decays. FIG. 3C shows the temporal dependence of the electrode's response to several glucose concentrations. The rates of the current decay are qualitatively consistence with the amount of glucose in the cell. In particular, the 1/e level is reached in 1 s, 1.2 s and 1.4 s for 100 zM, 300 zM and 500 zM, respectively. These short time constants reflect the minute amounts of glucose in the sample.

EXAMPLE 9

Detection Limit vs. $V_{ext}$ Measurement with Glucose

Figure 3D:
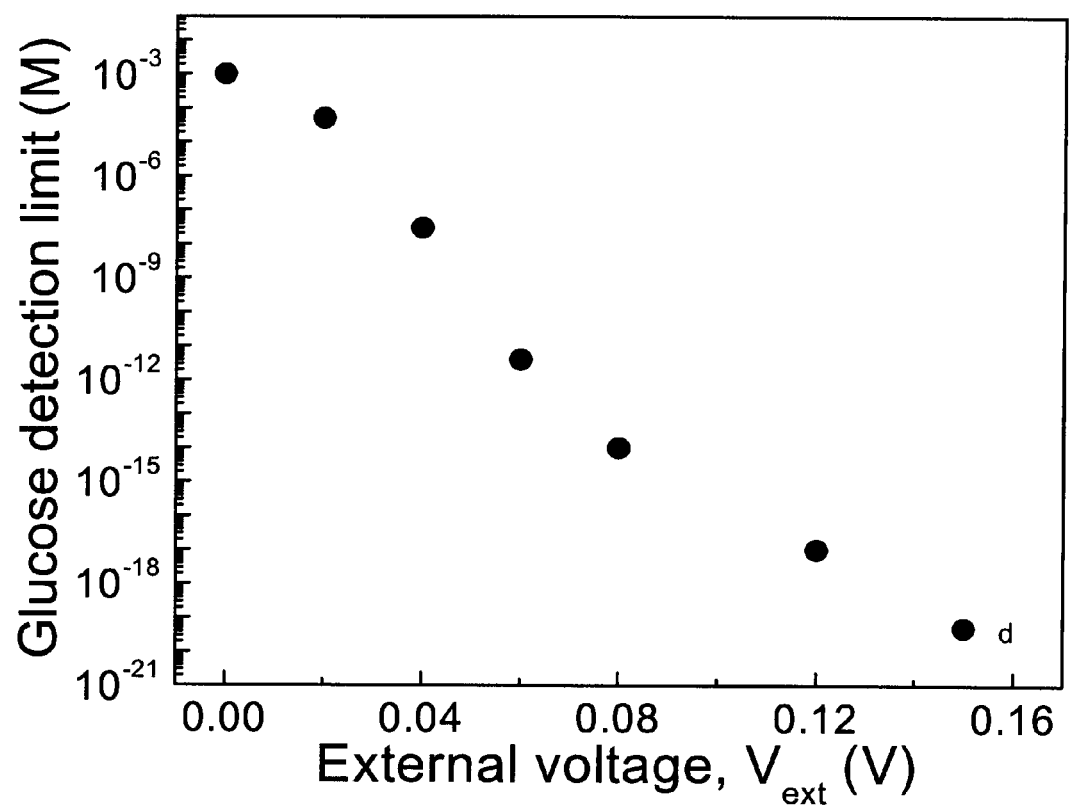
FIG. 3D shows the voltage-dependent glucose detection limit of the GOx-immobilized electrode according to one embodiment of the invention.

FIG. 3D shows the voltage-dependent glucose detection limit of the GOx-immobilized electrode. Two other GOx-immobilized electrodes showed the same relation. FIG. 3D shows that, by increasing $V_{ext}$ from 0 to 0.15 V, the glucose detection limit of the electrode was improved by 18 orders of magnitude. This detection limit (50 zM) was obtained using 3 different electrodes. The detection limit of 50 zM demonstrated is not limited by the field-related process, but is a result of the small volume (1 mL) of the electrochemical cell showing that further reduction in the analyte concentration will possibly result in no molecules in the cell.

EXAMPLE 10

Measurement ($V_{ext}$=0.15V) of Ethanol with Femto-Molar Concentrations

Figure 3E:
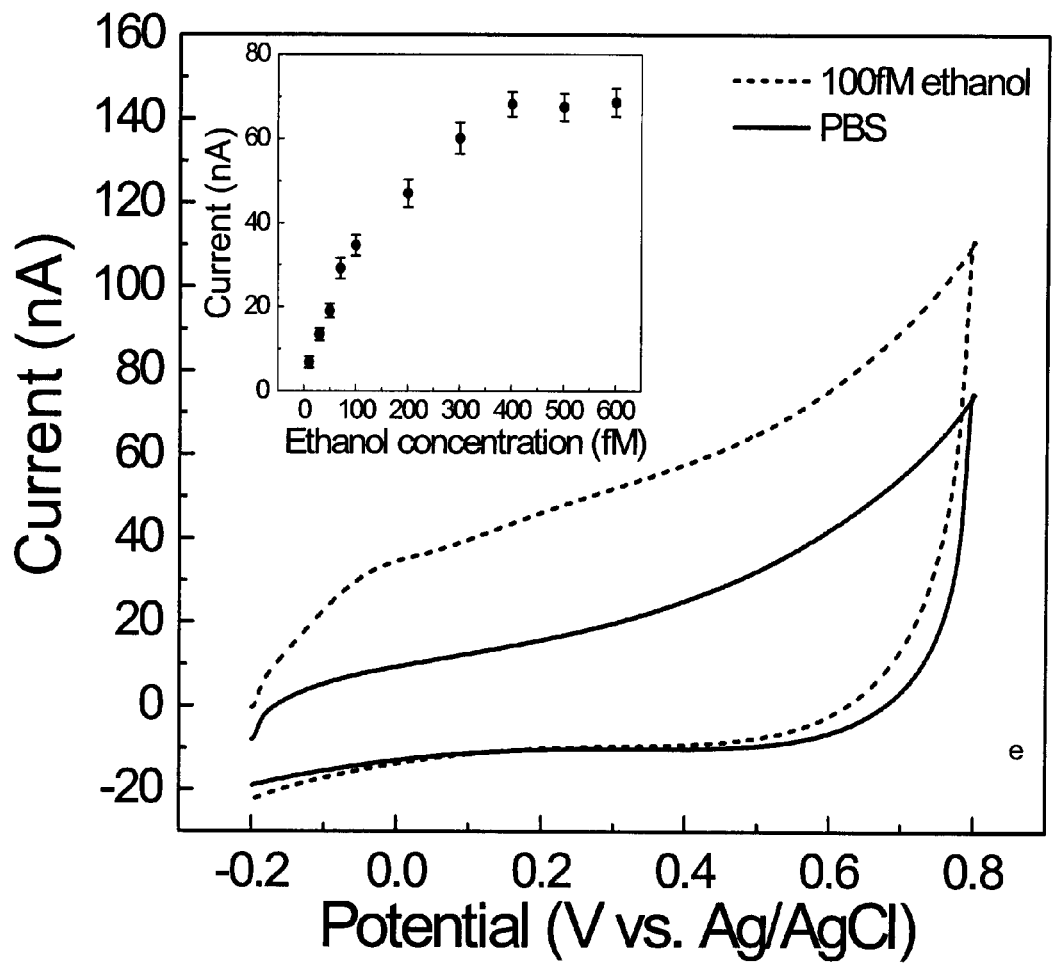
FIG. 3E shows the detection of ethanol in the femto-molar ($10^{-15}$ M) concentration range using ADH-immobilized HOPG electrode with $V_{ext}=0.15V$ according to one embodiment of the invention.

Similar voltage-induced improvement in analyte detection limit was also observed with ethanol-ADH system. Normally, ethanol detection using the ADH-immobilized HOPG edge-plane electrode is in the milli-molar range (result not shown). FIG. 3E shows the detection of ethanol in the femto-molar ($10^{-15}$ M) concentration range using ADH-immobilized HOPG electrode with $V_{ext}$=0.15V. The inset is the electrode's calibration curve for ethanol obtained at a potential of 0.7V.

The calibration curve in the inset indicates an ethanol detection limit of 10 fM with a detection resolution of 20 fM.

Examples 4-10 show that, by using $V_{ext}$, the current level of the detection signal for the wide range of analyte concentration studied can be controlled in the nano-ampere range for convenient electronic signal processing.

EXAMPLE 11

The Reversible Effect of $V_{ext}$ on Current

Figure 4:
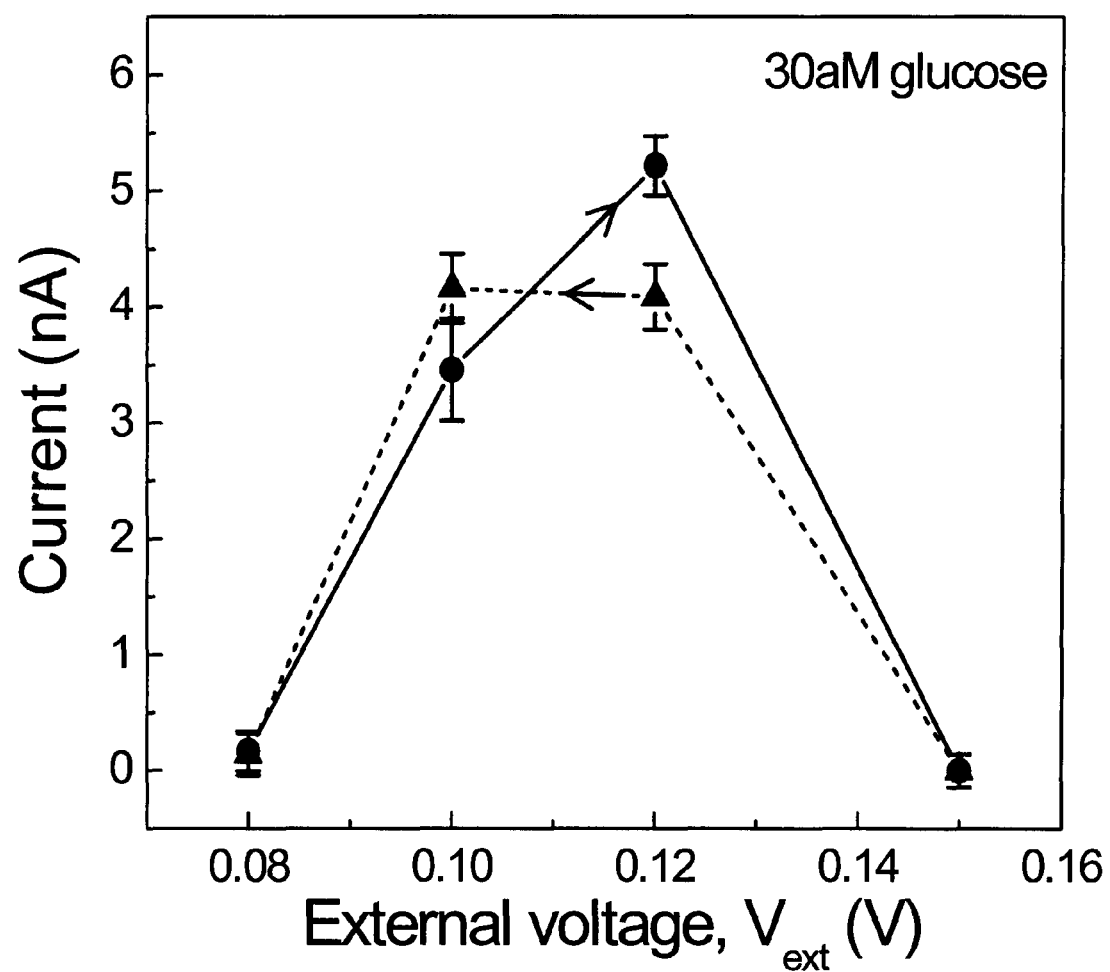
FIG. 4 shows the reversible dependence of the oxidation current of glucose on $V_{ext}$ demonstrated with 30 aM glucose according to one embodiment of the invention.

FIG. 4 shows the reversible effect of $V_{ext}$ on oxidation current. The glucose oxidation current is plotted versus $V_{ext}$ for 30 aM of glucose. The critical voltage Vc occurs at about 0.12V. The induced electric field did not produce permanent or irreversible effect on the catalytic activity of the immobilized GOx. In FIG. 4, the glucose oxidation currents of a GOx-immobilized electrode are plotted versus $V_{ext}$ for atto-molar range detection. The plots show that the current increases to a maximum value at $V_{ext}=0.12$ V, after which it decreases with further increase in $V_{ext}$. When $V_{ext}$ is reversed, the currents follow almost the same path to the original values as indicated by the arrows. This effect suggests that a certain amount of the GOx molecules can be temporarily "disabled" by the field due to an unknown mechanism, which occurs when the field becomes high enough. Nevertheless, this reversible characteristic is another manifestation that the field did not produce permanent detrimental effect on the enzyme.

EXAMPLE 12

The selectivity of GOx in the Presence of $V_{ext}$

Figure 5:
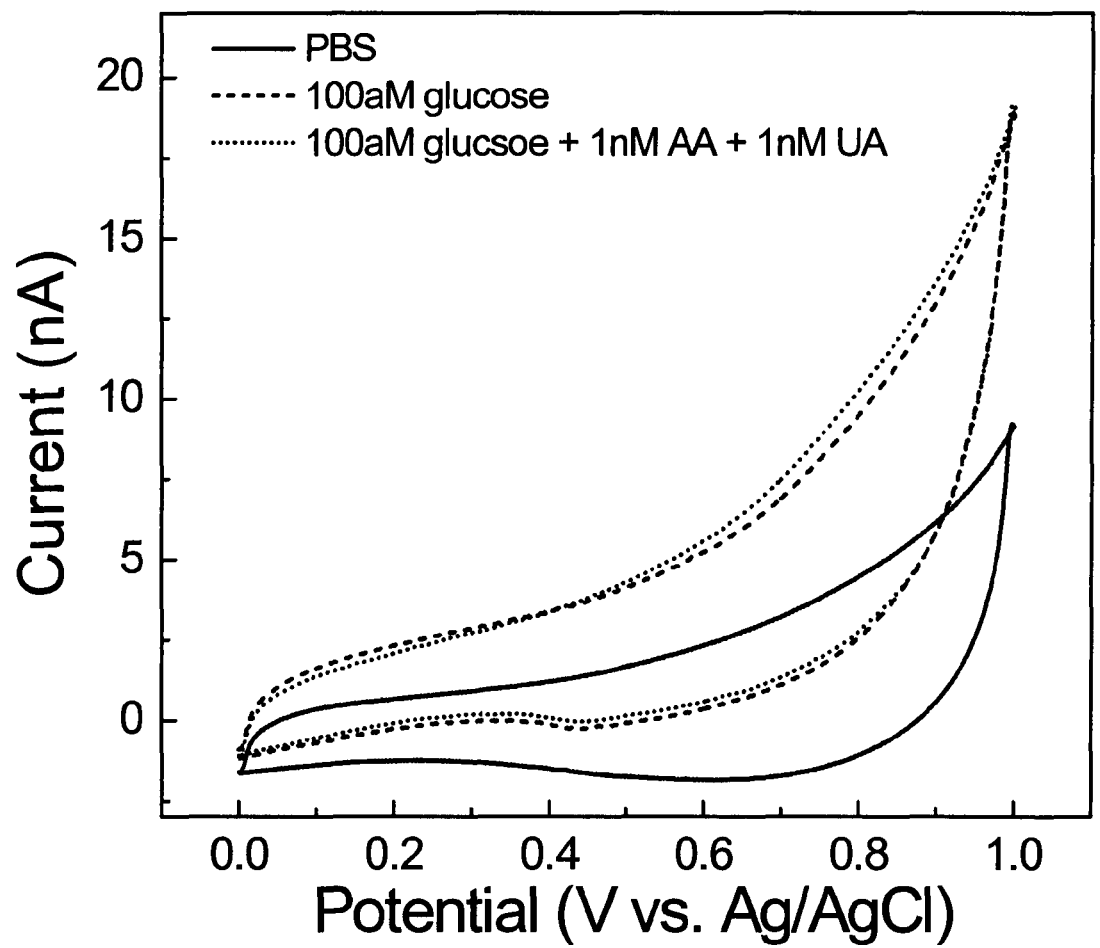
FIG. 5 shows the preserved enzymatic selectivity of GOx over glucose under the influence of the electric field ($V_{ext}=0.12V$) in the presence of interfering substances such as ascorbic acid and uric acid according to one embodiment of the invention.

The selectivity of GOx for glucose in the presence of the induced electric field has been tested. FIG. 5 shows the preserved enzymatic selectivity of GOx under the influence of the field. The CVs of a GOx-immobilized electrode were obtained with $V_{ext}=0.12$ V. In addition to producing biocatalytic currents in response to the presence of 100 aM of glucose only, the dash line CV, the electrode also shows CV with similar current levels, the dot line CV, in response to the presence of 100 aM of glucose in the presence of 1 nM of ascorbic acid (AA) and 1 nM of uric acid (UA).

It was observed that the enzyme's bio-specificity was preserved in the presence of the induced field. FIG. 5 shows that, with the field produced by $V_{ext}=0.12$ V, the response of a GOx-immobilized electrode to 100 aM of glucose is almost indistinguishable from that for which 1 nM of AA and 1 nM of UA, which are interfering substances in the body fluid, are present with the 100 aM glucose in the cell. Thus, the substance selectivity of GOx (enzyme's specificity for its analyte) has not been affected by the electric field in the presence of interfering substances, whose concentration are $10^7$ times higher than that of glucose (the analyte). At the physiological level, the ratio of these interfering substances to glucose is less than unity.

Without being bound to any particular theory, it is believed that the field modulates the electronic energy profile of the insulating barrier between the electrode and the active site of the sensing element such as oxidoreductase immobilized on the electrode. In this way, the electrode-active site charge transfer due to quantum mechanical tunneling can be enhanced so that the sensing/detecting sensitivity can be significantly increased.

Without being bound to any particular theory, it is believed that, for enzymes immobilized on an electrode, quantum mechanical tunneling gives rise to interfacial electron transfer. The field-induced enhancement of biocatalytic current observed here is likely to be the result of modified electronic energy profile of the tunnel barrier at the enzyme-electrode interface. The redox active site of an electroactive enzyme, i.e. the FAD of GOx or the $NAD^+$ of ADH, is surrounded by a polypeptide maze, making tunneling between this region and the electrode inefficient. An electric field with the correct polarity reduces the effective height of the tunnel barrier and therefore enhances the rate of tunneling. In an embodiment of the invention, applying a positive $V_{ext}$ with respect to the HOPG electrode lowers the height of the tunnel barrier (the insulating polypeptide maze). Thus, the observed enhancement in the oxidation current of the analytes (glucose and ethanol) and hence their significantly improved detection limit, is likely due to the result of the field-induced modification of the energy barrier on tunneling.

Without being bound to any particular theory, it is believed that the calibration curves in the insets of FIGS. 3A and 3E show current saturation due to the Michaelis-Menten kinetics. According to FIG. 2A, saturation should not occur at such low analyte concentration. This peculiar effect could be the result of the mechanism for the temporary loss of enzymatic activity. Since the enzymes carry charges on their surfaces, the field may re-orient them or change their conformation so that they are "disabled", the result of which being diminished catalytic activity or the interfacial tunneling or both. This is referred to as the "bad effect". Assuming the enzyme molecules have different state of immobilization in terms of orientation and the freedom to move on the electrode surface, which is likely to occur with the method of immobilization used here, the "bad effect" may "disable" the molecules with different field intensities produced by $V_{ext}$. Before the "bad effect" shows its effect, the "good effect", which is the field-induced modification of the tunnel barrier still enhances the oxidation current. As the field is increased, the tunnel current increases due to the "good effect". When the field is increased to a critical value Vc, a certain amount of enzyme molecules are "disabled" due to the "bad effect" and the number of functioning enzyme molecules on the electrode is reduced. In the milli-molar range of glucose, Vc occurs at about 0.02 V as shown in FIG. 2B. Suppose that the analyte concentration is now reduced to a lower range. If the field is further increased, more enzyme molecules will be "disabled". However, for the molecules that are not affected, the "good" effect still induces the enhancement in the tunnel current with the functioning enzyme molecules, and under the condition that the analyte concentration is low enough, a continuation of the region, in which the oxidation current increases with increasing $V_{ext}$, will occur beyond the Vc until a new and higher value of Vc is reached. FIG. 4 shows that in the atto-molar range, the new Vc is about 0.12 V. If the analyte concentration is increased, saturation in the oxidation current occurs due to the much reduced number of enzyme molecules.

Figure 6A:
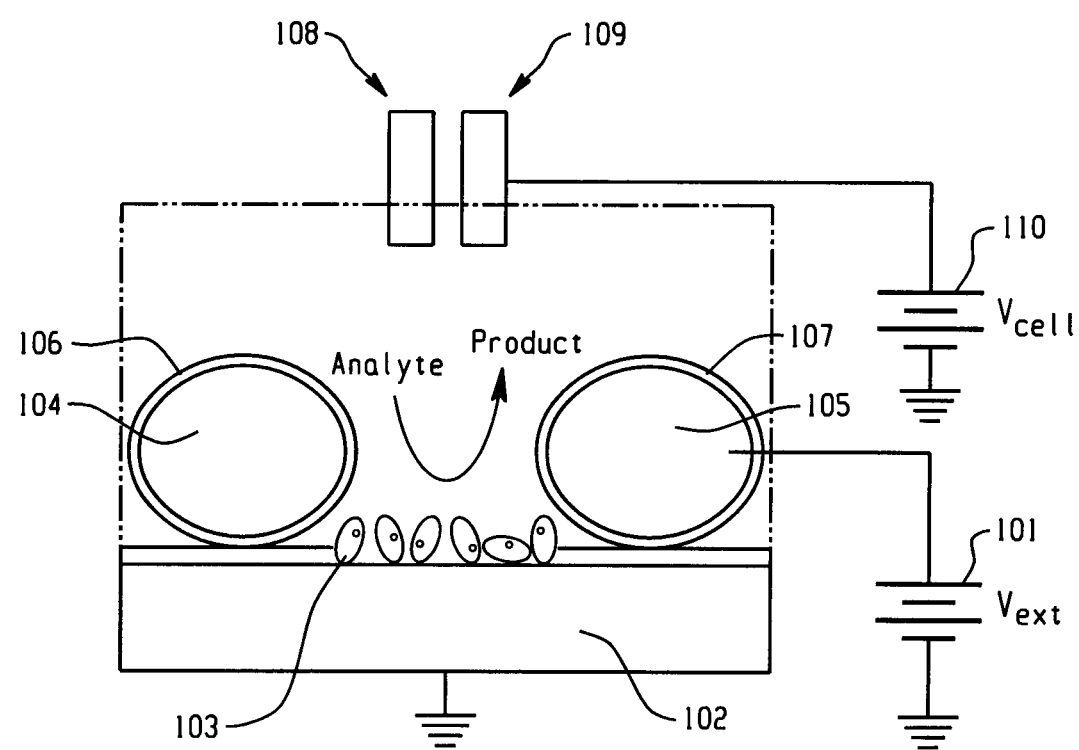
FIG. 6A shows the scheme of another cyclic voltammetry system according to one embodiment of the invention.

FIG. 6A is a schematic description of the sensing/detection system, as shown in FIG. 1A, with the cell potential $V_{cell}$ 110 connected between the working electrode 102 and the reference electrode 109. The counter electrode 108 is optional. The cell is modified with gating electrodes 104, 105 for applying a gating voltage $V_{ext}$ to the working electrode, upon which a redox enzyme (oxidoreductase) 103 is immobilized. As mentioned above, the gating electrodes 104, 105 used were copper wires with a thin layer of insulator 106, 107. $V_{ext}$ 101 is an external voltage source. Other geometries can be used as the gating electrodes. An example of the use of $V_{ext}$ is that when $V_{ext}$ is positive, negative charges are induced within the working electrode and positive ions in solution are induced at the solution-enzyme-electrode interface so that an electric field is established across the enzyme. This is seen in FIG. 6B, where the electric field is set up between positive charges and the transferring electrons residing at the enzyme's active sites.

The signal current of the sensing/detection system is due to the quantum mechanical tunneling of electrons through the non-electroactive region 112 of the polypeptide network between the active site of the enzyme and the electrode. The electronic energy profile of the polypeptide network (the tunnel barrier) of the enzyme at the enzyme-electrode interface can be modified by an electric field so that the tunneling rate is enhanced. The induced field penetrates the enzyme, lowering the effective height of the tunnel barrier and therefore increasing the electron tunnel rate and hence the current. The result of this process is an amplified signal current.

With reference again to FIG. 6B, the induced charges are located around the enzyme to set up the field. The enzyme catalyzes the oxidation of the analyte, resulting in the transfer of electrons to the active site. The effect of the $V_{cell}$ 110 and that of the induced electric field ($E_f$) is depicted using the interfacial electron energy profile as shown in FIGS. 6C, D.

Figure 6B:
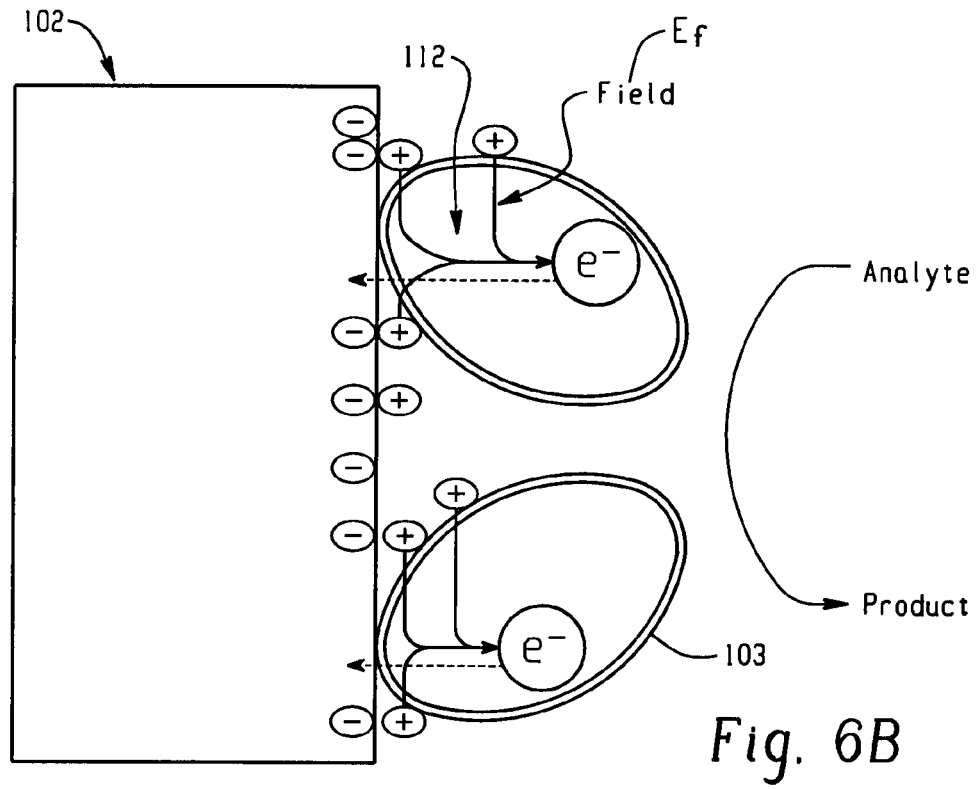
FIG. 6B shows a diagram of the enzyme-catalyzed oxidation of analyte according to one embodiment of the invention.
Figure 6C:
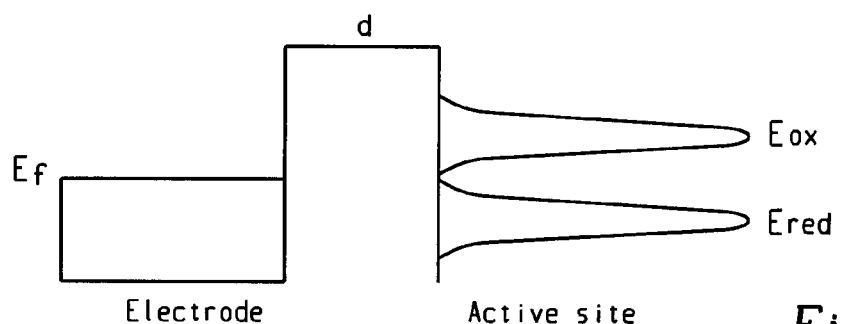
FIG. 6C shows an electron energy profile of the electrode at equilibrium according to one embodiment of the invention.
Figure 6D:
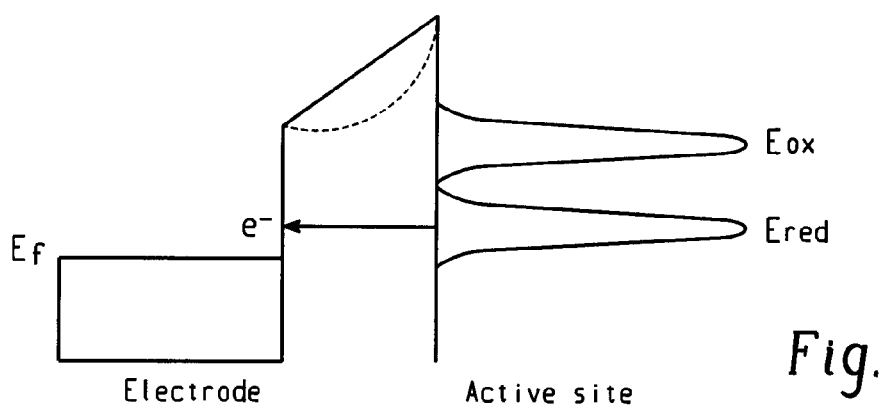
FIG. 6D shows an electron energy profile of the electrode subjected to positive cell potential and applied electric field according to one embodiment of the invention.

FIG. 6B further shows a conceptual electronic energy-band profile of the enzyme-electrode interface. At equilibrium, no electron transfer occurs between the active site and the electrode, since the most probable energy of the occupied quantum state of the active site, $E_{red}$, is below the Fermi energy, $E_F$, of the electrode. When the cell potential $V_{cell}$ is raised, oxidation of the enzyme occurs as electrons are energetically allowed to be transferred from the active site to the electrode. The electrode-active site system can be considered an acceptor-donor pair, wherein the electron transfer rate constant, $k_{et}$, depends on the distance d between the electrode and the active site, in accord with the expression: $k_{et} \propto \exp(-\beta d)$. The exponential dependence of $k_{et}$ on d effectively diminishes electron transfer when d is long enough. However, the rate constant $k_{et}$ also depends on the value of the attenuation coefficient, $\beta$, which is proportional to the square root of the tunnel barrier height ($\beta \propto (\Phi_B)^{1.2}$). For positive $V_{ext}$ 110, the induced electric field distorts the top of the tunnel barrier, as shown by the dotted curve in FIG. 6D, reducing the effective height of the barrier and, therefore, resulting in a smaller value of $\beta$ and therefore a larger value of $k_{et}$. Thus, electron conduction in the region between the active site and the electrode is enhanced, resulting in increased oxidation (signal) current of the analyte (signal amplification) and therefore lowered detection limit. A negative $V_{ext}$ will result in an upward bending of the top of the tunnel barrier, resulting in a decrease in the signal current.

Figure 7:
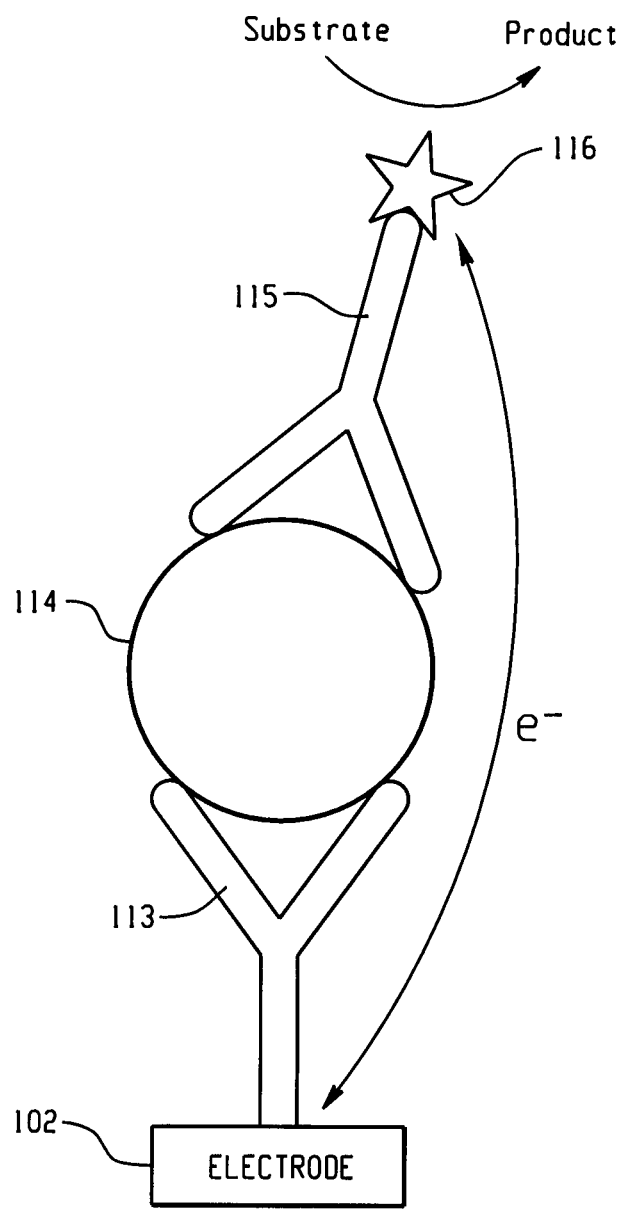
FIG. 7 shows a sandwich amperometric immuno-sensing structure according to one embodiment of the invention.

The featured detection technique has been applied to amperometric immuno-sensing systems. FIG. 7 shows the essential component of the amperometric immuno-sensing system—the antibody-antigen-antibody (Ab-Ag-Ab) sandwich structure. The primary antibody 113 is immobilized on the working electrode 102. The binding of the antigen 114 to the primary antibody 113, and subsequently to the secondary antibody 115 is due to immunological interaction. The secondary antibody 115 is labeled with a redox enzyme 116 (oxidoreductase). The redox enzyme (oxidoreductase) is immobilized on the working electrode via the Ab-Ag-Ab structure. The induced electric field modifies the energy profile of the Ab-Ag-Ab structure (non-electroactive) in order to enhance the electron transfer through this interfacial region. The resulting enhanced electron transfer will significantly lower the detection limit of antigens. The detection of PSA, CA 125 and E. coli have been carried out as examples of the feasibility of this detection approach.

EXAMPLE 13

The Detection of Prostate Specific Antigen (PSA)

Figure 8:
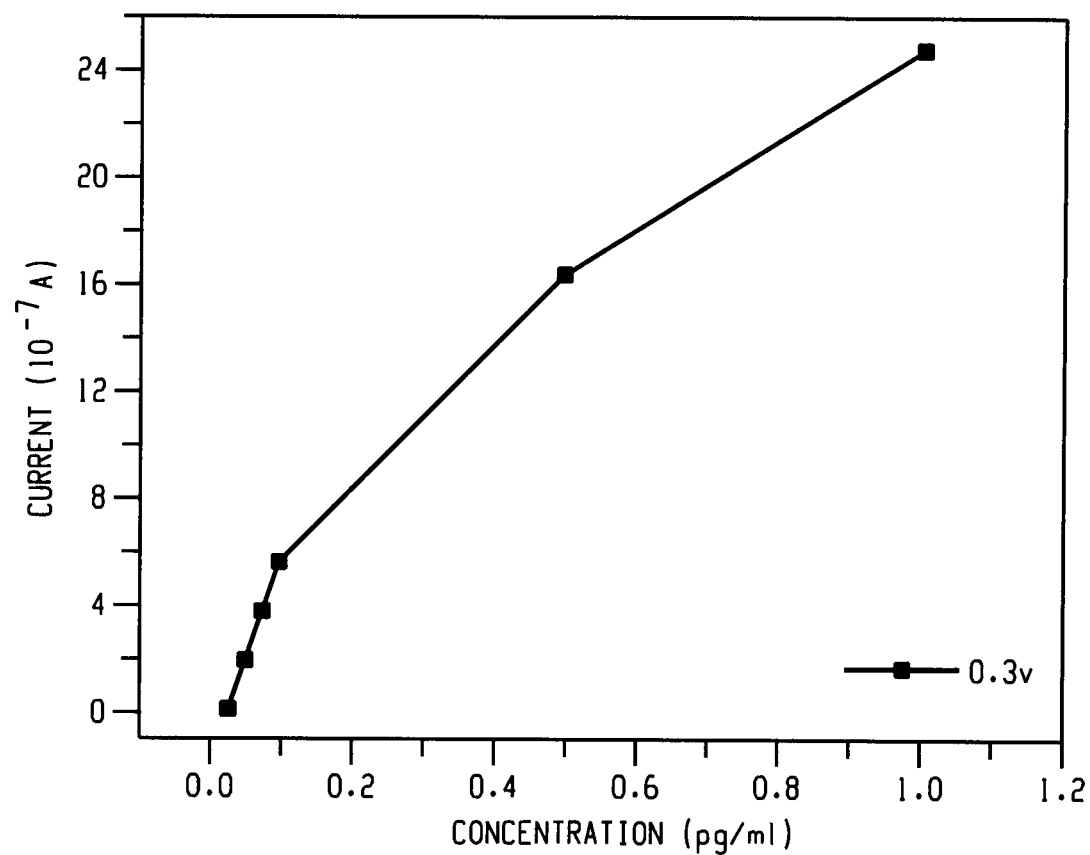
FIG. 8 shows a PSA calibration curve with regard to Example 13 according to one embodiment of the invention.

In the detection of prostate specific antigen (PSA), a protein biomarker of prostate cancer, the Ab-PSA-Ab sandwich structure was formed on a gold electrode. Horseradish peroxidase (HRP), a redox enzyme, was used to label the secondary Ab. The primary Ab was immobilized on the gold electrode, which was modified with a self-assembled monolayer of co-mercaptohexadecanoic acid. Other methods for hosting the primary Ab and hence the Ab-PSA-Ab (enzyme) can also be used to immobilize the redox enzyme (oxidoreductase) on the electrode. $H_2O_2$ was injected into the electrochemical cell to initiate the electrode current as the result of the reduction of $H_2O_2$ catalyzed by HRP. The reduction current of $H_2O_2$ was measured as the detection signal. A detection limit of 30 femto gram ($10^{-15}$ g) of PSA per ml of PSA in serum samples was obtained by applying $V_{ext}$. FIG. 8 provides PSA calibration curve in the femto gram/ml range as the result of using $V_{ext}$=0.3 volt. The upper end of the detection was 40 nanogram/ml of PSA (not shown in figure), which could be obtained with or without $V_{ext}$. The detection signal was also taken as the peak current of the reduction peak of the immobilized HRP without adding $H_2O_2$ to the cell. This example represents a reagentless detection approach. No substrate of the enzyme was used.

EXAMPLE 14

The detection of Carcinoma Antigen 125 (CA125)

In the detection of carcinoma antigen 125 (CA125), a biomarker of ovarian cancer, CA 125 was immobilized using incubation on a graphite electrode, whose surface was modified with a layer of Nafion, carbon nanotubes and glutaraldehyde. HRP-labeled Ab was then released to the electrode to form the CA125-Ab(HRP) structure, which immobilized HRP on the electrode. The reagentless approach as described above was used in obtaining the detection signal.

Figure 9A:
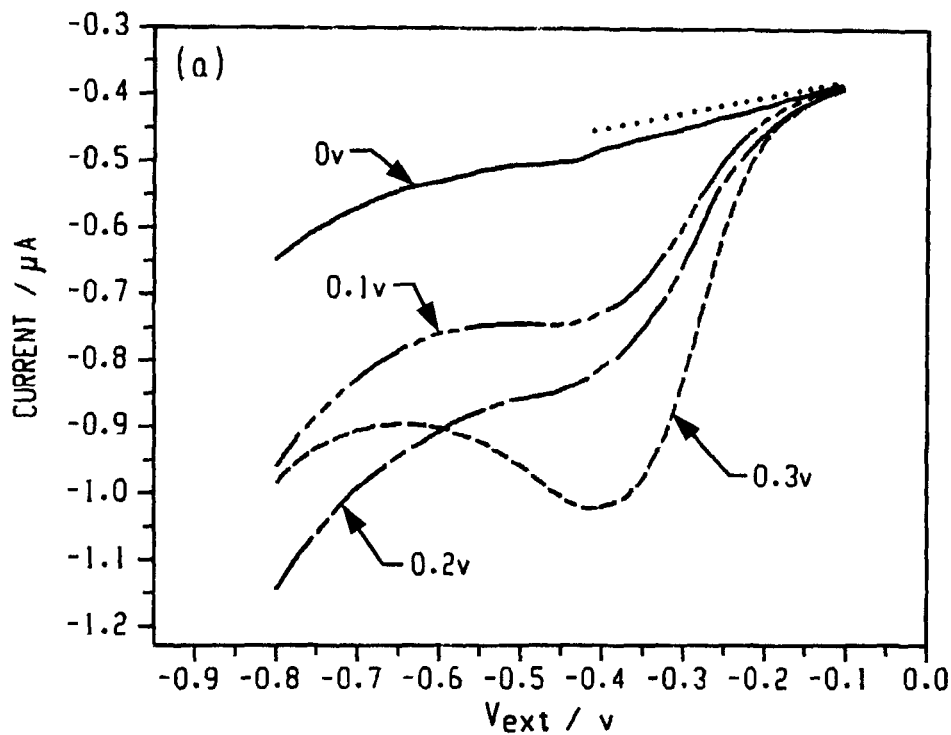
FIG. 9A shows LVs of CA-125-immobilized on a detecting electrode incubated with 200 U/ml CA-125 at $V_{ext}=0$, 0.1, 0.2 and 0.3 and corresponding reduction peak currents according to one embodiment of the invention.
Figure 9B:
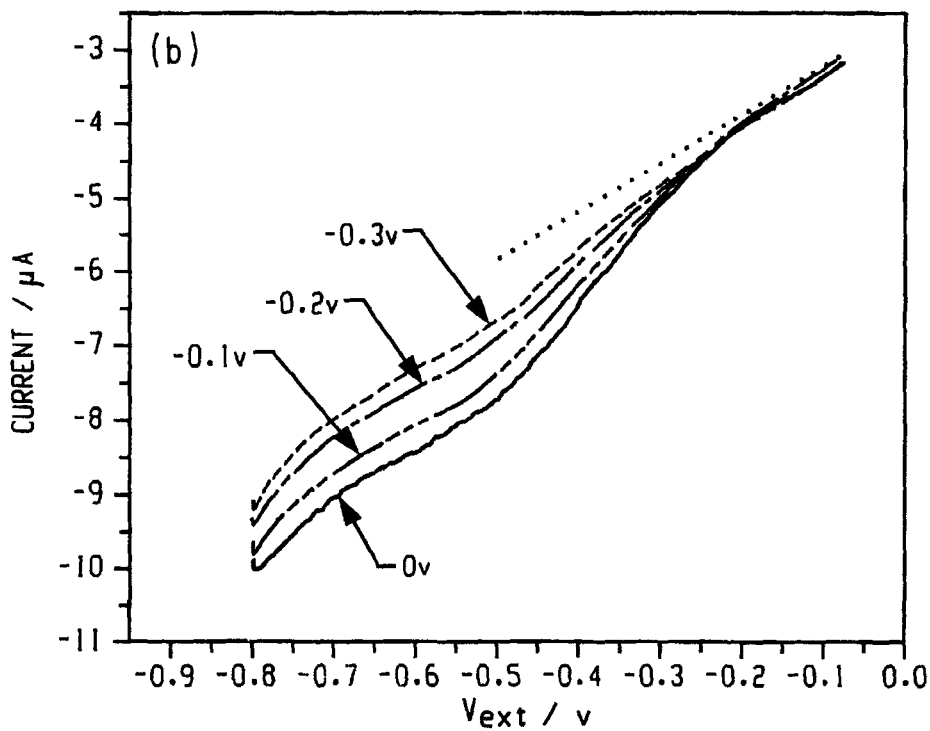
FIG. 9B shows the effect of negative polarity of $V_{ext}$ on the LVs obtained using the set up of FIG. 9A according to one embodiment of the invention.

The effect of applying $V_{ext}$ on the detection signal was studied. FIG. 9A shows four linear voltammograms (LVs) obtained with a detecting electrode, which was incubated with 200 U/ml CA-125. The four LVs were obtained with $V_{ext}$=0, 0.1, 0.2, 0.3 V, respectively, and the corresponding peak currents of the reduction peak of HRP were 0.04, 0.3, 0.4, and 0.58 µA as measured using the baseline. FIG. 9A shows that $V_{ext}$ caused amplification of the signal current (the peak current), and is consistent with the principle of the featured detection technique, i.e., the increase in the signal current caused by applying $V_{ext}$ in the positive polarity was due to the reduction of the height of the tunnel barrier between the active site of the enzyme and the electrode. Evidence further supporting this mechanism was observed by reversing the polarity of $V_{ext}$. A negative $V_{ext}$ reversed the direction of the induced field and therefore increased the effective height of the tunnel barrier. FIG. 9B shows the effect of increasing $V_{ext}$ in the negative polarity on the signal current. The LVs were obtained with progressively increasing $V_{ext}$ in the negative polarity. Also shown is the baseline. The decrease in the signal supports the scenario of a modified tunnel barrier.

Figure 10A:
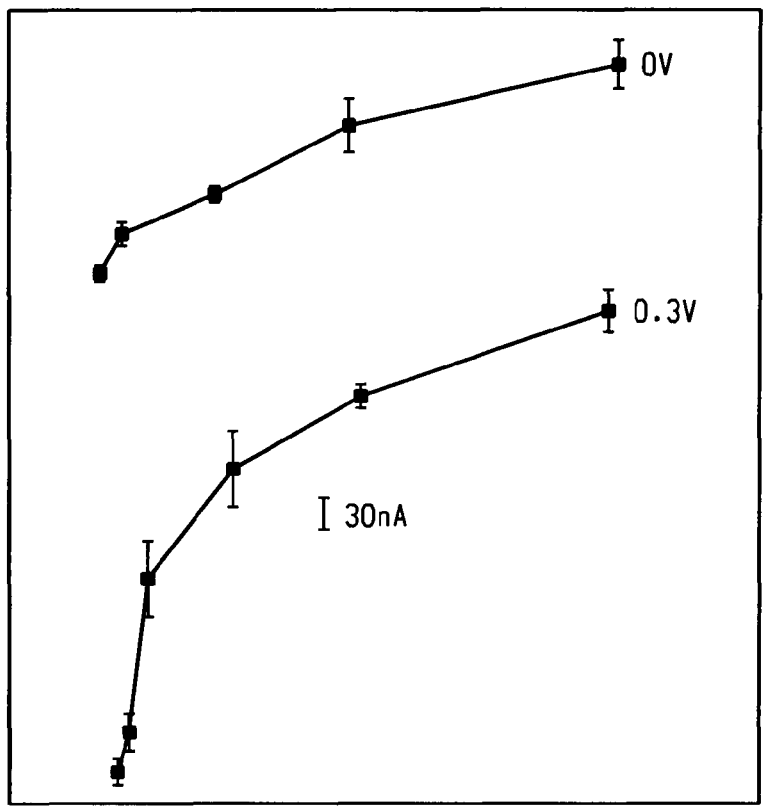
FIG. 10A shows the CA125 calibration curves of the detection system obtained with $V_{ext}=0$ and 0.3 using six detecting electrodes (3, 7, 15, 50, 100, 200 U/ml) according to one embodiment of the invention.
Figure 10B:
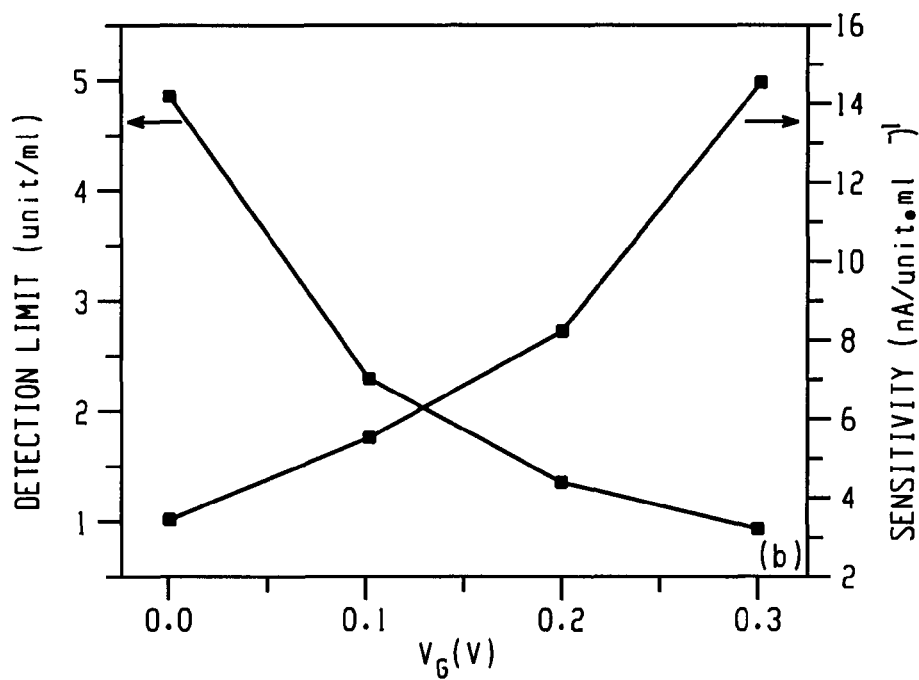
FIG. 10B shows dependency of sensitivity and detection limit of the system used in FIG. 9A on $V_{ext}$ according to one embodiment of the invention.

The detection system's calibration curves for CA 125 obtained with $V_{ext}$=0 V and 0.3 V using six detecting electrodes (3, 7, 15, 50, 100, 200 U/ml) are shown in FIG. 10A. FIG. 10B shows the dependences of the sensitivity and the detection limit of the detection system on $V_{ext}$. The sensitivity is increased from 1 to about 15 nA/U·ml$^{-1}$ as $V_{ext}$ is increased from 0V to 0.3 V. The 5-fold increase in sensitivity is significant because it allows the detection limit to be lowered from 4.9 U/ml to 0.9 U/ml.

EXAMPLE 15

The Detection of Bacteria E. coli

Figure 11:
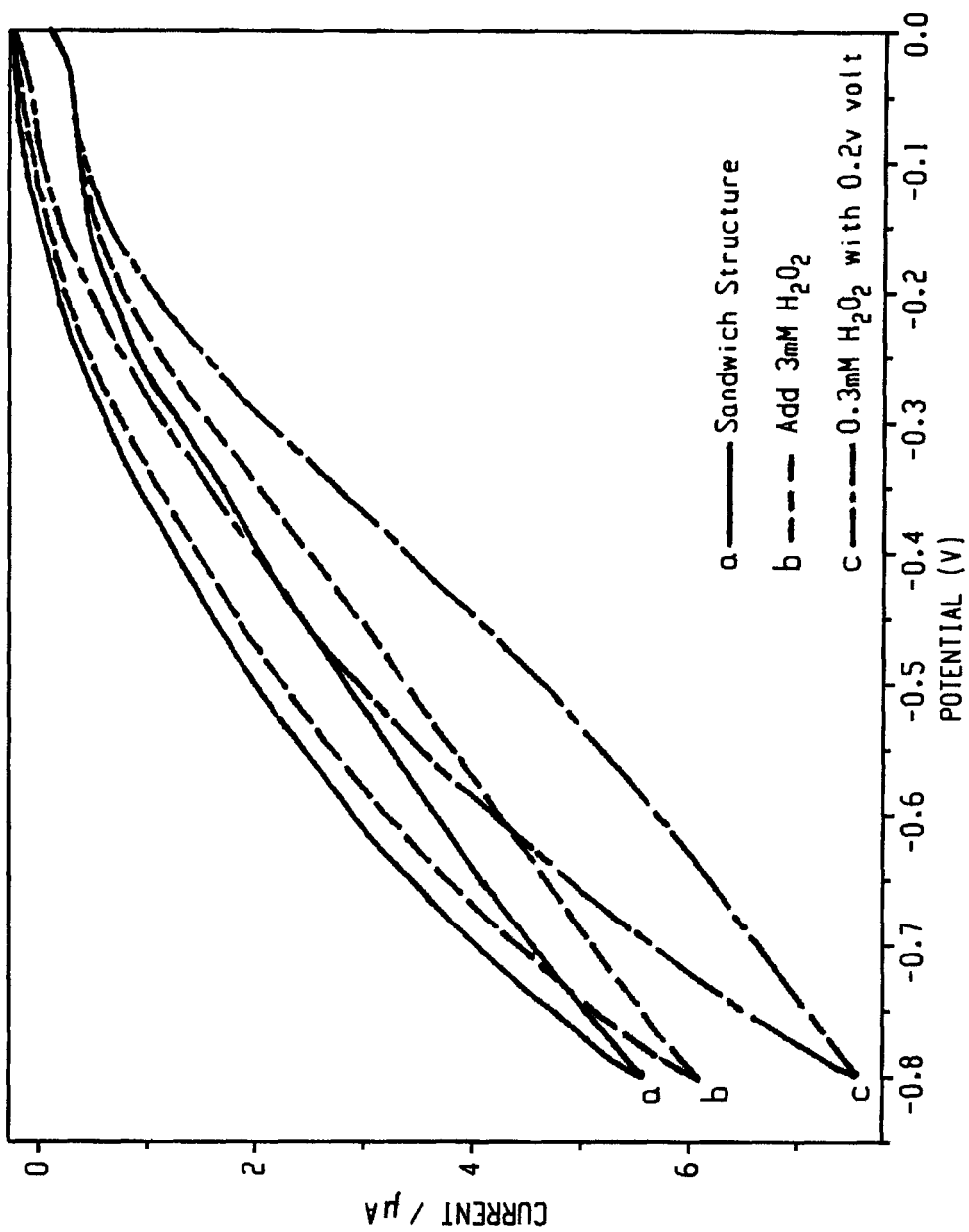
FIG. 11 shows CVs of an electrode immobilized with the Ab-E. coli-Ab (HRP) structure according to one embodiment of the invention.

To show the feasibility of the detection technique for the detection of bacteria, the detection of E. coli was carried out, again using the sandwich structure Ab-*E.coli*-Ab(HRP). In FIG. 11, Curve a is the cyclic voltammogram (CV) of an electrode having the Ab-*E.coli*-Ab(HRP) sandwich structure on its surface measured in a buffer solution. Curve b shows the electrode's response to 3 mM $H_2O_2$. Curve c shows the electrode's response to 3 mM $H_2O_2$ with the application of 0.2V. The results indicate the detection of *E. coil* with amplified signal current in accord with the foregoing. As such, the application of the technique is shown as a viable option for bacteria detection at very low levels.

Exemplary embodiments have been described herein. They include all systems and methods in accord with the preferred embodiments, and the application of such systems/methods to the control and/or detection of electron transfer across electrode-material-solution interfaces, or electrode-solution interfaces wherein a material of interest is disposed in solution, using a voltage generator in accord herewith. Such systems and methods find application in a variety of technologies, for example as shown hereinabove, to enhance the anode and/or cathode reaction kinetics of a fuel cell, or to enhance electron transfer during natural or artificial photosynthesis. Obviously, modifications and alterations will occur to others upon reading and understanding the preceding detailed description.

The invention claimed is:

1. An amperometric immuno-sensing system embodied in the form of an electrochemical cell system, the system comprising a working electrode, a reference electrode, and a counter electrode connected as a three-electrode cell, an enzyme-labeled antigen or an enzyme-labeled antibody, and an additional electrode, wherein the additional electrode is operatively connected to an external voltage source, wherein the enzyme-labeled antigen or the enzyme-labeled antibody is immobilized on the working electrode; and wherein the additional electrode is configured to apply an external voltage from the external voltage source between the additional electrode and the working electrode to induce an electric field, at least a portion of an interface between the enzyme-labeled antigen or the enzyme-labeled antibody and the working electrode being permeated by the electric field.

2. The amperometric immuno-sensing system according to claim 1, further including a gating electrode.

3. The system of claim 2, wherein the gating electrodes are coated with insulators.

4. The amperometric immuno-sensing system according to claim 1, in which the external voltage ranges from about 0.001 volt to about 5 volt.

5. The amperometric immuno-sensing system according to claim 4, in which the external voltage ranges from about 0.005 volt to about 0.5volt.

6. The amperometric immuno-sensing system according to claim 5, in which the external voltage ranges from about 0.01 volt to about 0.2 volt.

7. The amperometric immuno-sensing system according to claim 4, wherein the system relies on the enzymatic activity of the enzyme.

8. The amperometric immuno-sensing system according to claim 1, wherein the working electrode is a modified graphite electrode.

9. The system of claim 1, wherein the system does not comprise mediators.

10. A voltammetry/amperometry system comprising a working electrode, a reference electrode, and a counter electrode connected as a three-electrode cell, an oxidoreductase, and an additional electrode, wherein the additional electrode is operatively connected to an external voltage source, wherein the oxidoreductase is immobilized on the working electrode; and wherein the additional electrode is configured to apply a voltage from the external voltage source between the additional electrode and the working electrode to induce an electric field, at least a portion of an interface between the oxidoreductase and the working electrode being permeated by the electric field; wherein the voltage source is configured to generate a $V_{ext}$ from about 0.001 volt to about 2 volt.

11. The voltammetry/amperometry system according to claim 10, in which the voltage source is configured to generate a $V_{ext}$ from about 0.005 volt to about 0.5 volt.

12. The voltammetry/amperometry system according to claim 11, in which the voltage source is configured to generate a Vext from about 0.01 volt to about 0.2 volt.

13. The voltammetry/amperometry system according to claim 10, in which the oxidoreductase comprises an enzyme that catalyzes the oxidation or reduction of an analyte or reactant resulting in charge transfer across the interface between the oxidoreductase and the working electrode.

14. The voltammetry/amperometry system according to claim 10, in which the oxidoreductase comprises a biological, organic or inorganic electro-active material that induces charge transfer at the interface between the electrode and the electro-active material.

15. The voltammetry/amperometry system according to claim 10, in which the oxidoreductase comprises an enzyme that catalyzes the transfer of electrons from a reductant to an oxidant.

16. The voltammetry/amperometry system according to claim 15, in which the reductant comprises CH—OH group; aldehyde or oxo; CH—CH group; CH—NH2group; CH—NH group; NADH or NADPH; sulfur group; heme group; diphenols; hydrogen; CH or CH2groups; metal ions; iron-sulfur proteins; reduced flavodoxin; phosphorus or arsenic; or X—H and Y—H.

17. The voltammetry/amperometry system according to claim 15, in which the oxidant comprises peroxide or superoxide radical.

18. The voltammetry/amperometry system according to claim 10, in which the oxidoreductase comprises glucose oxidase enzyme (GOx).

19. The voltammetry/amperometry system according to claim 10, in which the oxidoreductase comprises alcohol dehydrogenase.

20. The voltammetry/amperometry system according to claim 10, wherein the electric field has a field intensity of up to about 100 volt/cm for inorganic material.

21. The voltammetry/amperometry system according to claim 10, wherein the electric field has a field intensity of up to 10 volt/cm for biochemical material such as oxidoreductase.

22. The voltammetry/amperometry system according to claim 21, in which the field intensity is from about 0.2 volt/cm to about 6.0 volt/cm.

23. The voltammetry/amperometry system according to claim 22, in which the field intensity is from about 0.4 volt/cm to about 3.0 volt/cm.

24. The voltammetry/amperometry system according to claim 10, which has a detection limit in the magnitude of zepto-molar ($10^{'21}$ M) range with zepto molar detection resolution.

25. A biosensor comprising the voltammetry/amperometry system according to claim 10.

26. An electrochemical sensor comprising the voltammetry/amperometry system according to claim 10.

27. The system of claim 10, wherein the system does not comprise mediators.

* * * * *